US008481035B2

(12) United States Patent
Schaeffer et al.

(10) Patent No.: US 8,481,035 B2
(45) Date of Patent: Jul. 9, 2013

(54) METHODS FOR TREATING CHRONIC PELVIC PAIN SYNDROME WITH ANTIBODIES THAT BINDS MCP-1 OR MIP-1A

(75) Inventors: Anthony J. Schaeffer, Hinsdale, IL (US); David Klumpp, Chicago, IL (US); Praveen Thumbikat, Morton Grove, IL (US)

(73) Assignee: Northwestern University, Evanston, IL (US)

( * ) Notice: Subject to any disclaimer, the term of this patent is extended or adjusted under 35 U.S.C. 154(b) by 81 days.

(21) Appl. No.: 12/881,664

(22) Filed: Sep. 14, 2010

(65) Prior Publication Data

US 2011/0014205 A1    Jan. 20, 2011

Related U.S. Application Data

(63) Continuation-in-part of application No. 11/115,747, filed on Apr. 27, 2005, now Pat. No. 7,794,949.

(60) Provisional application No. 60/565,768, filed on Apr. 27, 2004.

(51) Int. Cl.
*A61K 39/395* (2006.01)
*C07K 16/24* (2006.01)
*C12P 21/08* (2006.01)

(52) U.S. Cl.
USPC .................. 424/145.1; 424/130.1; 424/141.1; 530/387.1; 530/388.1; 530/388.23

(58) Field of Classification Search
None
See application file for complete search history.

(56) References Cited

U.S. PATENT DOCUMENTS

| 6,011,052 | A  | 1/2000  | Padia et al. |
| 6,180,355 | B1 | 1/2001  | Alexander |
| 7,138,230 | B2 | 11/2006 | Hu |
| 7,202,343 | B2 | 4/2007  | Gudas |
| 2002/0160415 | A1 | 10/2002 | Neely et al. |
| 2003/0083231 | A1 | 5/2003  | Ahlem et al. |

FOREIGN PATENT DOCUMENTS

| WO | 97/44329 | 11/1997 |
| WO | 98/06703 | 2/1998 |
| WO | 99/07351 | 2/1999 |
| WO | 99/07678 | 2/1999 |
| WO | 99/25686 | 5/1999 |
| WO | 99/40913 | 8/1999 |
| WO | 99/40914 | 8/1999 |
| WO | 99/46991 | 9/1999 |
| WO | 00/46196 | 8/2000 |
| WO | 00/69815 | 11/2000 |
| WO | 00/69820 | 11/2000 |
| WO | 01/89565 | 11/2001 |

OTHER PUBLICATIONS

Alexander, et al., "Chronic Prostatitis: Results of an Internet Survey," Urology, 48:568-574 (1996).
Altman et al., "Statistics Notes: Diagnostic tests 2: predictive values," BMJ 309:102 (1994).
Altman et al., "Statistics Notes: Diagnostic tests 3: receiver operating characteristic plots," BMJ 309:188 (1994).
Andres, et al., "Mice with a selective deletion of the CC chemokine receptors 5 or 2 are protected from dextran sodium sulfate-mediated colitis: lack of CC chemokine receptor 5 expression results in a NK1.1+ lymphocyte-associated Th2-type immune response in the intestine," J. Immunol, 164, 6303-6312 (2000).
Antoniades, et al., "Expression of monocyte chemoattractant protein 1 mRNA in human idiopathic pulmonary fibrosis," Proc. Natl. Acad. Sci. USA , 89, 5371-5375 (1992).
Baba et al, "A small-molecule, nonpeptide CCR5 antagonist with highly potent and selective anti-HIV-1 activity," PNAS, 96, 5698-56703 (1999).
Bahnson, "Elevation of prostate specific antigen from bacillus Calmette-Guerin-induced granulomatous prostatitis," J Urology, 146, pp. 1368-1369 (1991).
Bast et al., "Translational Crossroads for Biomarkers," Clin Cancer Res., 11:6103-6108 (2005).
Belperio, et al., "Critical role for the chemokine MCP-1/CCR2 in the pathogenesis of bronchiolitis obliterans syndrome," J. Clin. Invest, 108, 547-556 (2001).
Berman, et al., "Localization of monocyte chemoattractant peptide-1 expression in the central nervous system in experimental autoimmune encephalomyelitis and trauma in the rat," J. Immunol., 156, 3017-3023 (1996).
Bonini, et al., "Cloning, expression, and chromosomal mapping of a novel human CC-chemokine receptor (CCR10) that displays high-affinity binding for MCP-1 and MCP-3," DNA Cell Biol., 16, 1249-1256 (1997).
Boring, et al, "Decreased lesion formation in CCR2-/- mice reveals a role for chemokines in the initiation of atherosclerosis," Nature, 394, 894-897 (1998).
Boring, et al., "Impaired monocyte migration and reduced type 1 (Th1) cytokine responses in C-C chemokine receptor 2 knockout mice," J. Clin. Invest, 100, 2552-2261 (1997).
Carter, "Chemokine receptor antagonism as an approach to anti-inflammatory therapy: 'just right' or plain wrong?," Current Opinion in Chemical Biology, 6(4), 510-525 (2002).
Charo, et al., "Molecular cloning and functional expression of two monocyte chemoattractant protein 1 receptors reveals alternative splicing of the carboxyl-terminal tails," Proc. Natl. Acad. Sci. USA 1994, 91, 2752-2756.
Combadiere, et al., "Cloning and functional expression of a human eosinophil CC chemokine receptor," J. Biol. Chem., 270, 1 6491-1 6494 (1995).
Connor, et al., "Change in coreceptor use correlates with disease progression in HIV-1—infected individuals," J. Exp. Med., 185, 621-628 (1997).

(Continued)

*Primary Examiner* — Christine J Saoud
*Assistant Examiner* — Jon M Lockard
(74) *Attorney, Agent, or Firm* — Casimir Jones

(57) ABSTRACT

The present invention provides methods and compositions for treating chronic pelvic pain syndrome. In particular, the present invention provides methods and compositions for treating chronic pelvic pain syndrome with an agent that targets MCP-1, MIP-1α, or the CCR-2 receptor.

14 Claims, 8 Drawing Sheets

OTHER PUBLICATIONS

Dallal "P Values" and "Why P=0.05?" In "The Little Handbook of Statistical Practice," retrieved from http://www.tufts.edu/~gdallal/LHSP.HTM on Aug. 21, 2008, Copyright (c) 2000 Gerard E. Dallal.
Deleuran, et al., "Localization of monocyte chemotactic and activating factor (MCAF/MCP-1) in psoriasis," J. Dermatol. Sci., 13, 228-236 (1996).
Desireddi et al., 2008, "Monocyte chemoattractant protein-1 and macrophage inflammatory protein-1alpha as possible biomarkers for the chronic pelvic pain syndrome," J Urol., 179:1857-1863.
Dhundee et al., "An immunohistological study of granulomatous prostatitis," Histopathology, 18, 435-441 (1991).
Doranz, et al., "A dual-tropic primary HIV-1 isolate that uses fusin and the beta-chemokine receptors CKR-5, CKR-3, and CKR-2b as fusion cofactors," Cell, 85, 1149-1158 (1996).
Dower et al., "Detection and characterization of high affinity plasma membrane receptors for human interleukin 1," J Exp Med., 162, 501-515 (1985).
Fife, et al., "CC chemokine receptor 2 is critical for induction of experimental autoimmune encephalomyelitis," J. Exp. Med., 192, 899-906 (2000).
Forbes et al., "CCR2B receptor antagonists: conversion of a weak HTS hit to a potent lead compound," Bioorg. Med. Chem. Lett., 10,1803-1806, 2000.
Gillitzer, et al., "MCP-1 mRNA expression in basal keratinocytes of psoriatic lesions," J. Invest. Dermatol., 101, 127-131 (1993).
Gong et al., "An antagonist of monocyte chemoattractant protein 1 (MCP-1) inhibits arthritis in the MRL-Ipr mouse model," J Exp Med 186, 131-137 (1997).
Gonzalo, et al., "The coordinated action of CC chemokines in the lung orchestrates allergic inflammation and airway hyperresponsiveness," J. Exp. Med., 188, 157-167 (1998).
Gosling, et al., "MCP-1 deficiency reduces susceptibility to atherosclerosis in mice that overexpress human apolipoprotein B," J. Clin. Invest., 103, 773-778 (1999).
Grimm, et al., "Enhanced expression and production of monocyte chemoattractant protein-1 in inflammatory bowel disease mucosa.," J. Leukoc. Biol., 59, 804-812 (1996).
Gu, et al., "Absence of monocyte chemoattractant protein-1 reduces atherosclerosis in low density lipoprotein receptor-deficient mice," Mol. Cell, 2, 275-281 (1998).
Haringman et al., "A randomized controlled trial with an anti-CCL2 (anti-monocyte chemotactic protein 1) monoclonal antibody in patients with rheumatoid arthritis," Arthritis Rheum, 54, p. 2387-2392 (2006).
Haworth et al., "Cytokine and Anti-Cytokine Therapy," The Cytokine Handbook, Thomson, Angus ed., pp. 777-801, (1998).
Horuk, "Molecular properties of the chemokine receptor family," Trends Pharm. Sci., 15, 159-165 (1994).
Hosmer and Lemeshow, Applied Logistic Regression, John Wiley & Sons, Inc., New York, NY, 1989.
Iarlori et al., "Interferon beta-1b modulates MCP-1 expression and production in relapsing-remitting multiple sclerosis," J Neuroimmunol, 123,170-179 (2002).
Information Hyperlinked over Proteins (iHOP), entry for CCL2, downloaded from http://www.ihop-net.org/UniPub/iHOP/gs/92036 .html on Oct. 15, 2007.
Information Hyperlinked over Proteins (iHOP), entry for CCL3, downloaded from http://www.ihop-net.org/UniPub/iHOP/gs/124501.html on Oct. 15, 2007.
Izikson, et al., "Resistance to experimental autoimmune encephalomyelitis in mice lacking the CC chemokine receptor (CCR)2," J. Exp. Med., 192, 1075-1080 (2000).
Janeway, et al., Immunobiology: the Immune System in Heatlh and Disease (1999), Elsevier Science Ltd/Garland Publishing, new York, NY, Fourth Edition, p. 41.
Jang, T.L. and Schaeffer, A.J., "The Role of Cytokines in Prostatitis," (2003) World J. Urol 21:95-99.
Jones, et al., "Potential role of monocyte chemoattractant protein 1/JE in monocyte/macrophage-dependent IgA immune complex alveolitis in the rat," J. Immunol., 149, 2147-2154 (1992).
Kennedy, et al., "Acute and relapsing experimental autoimmune encephalomyelitis are regulated by differential expression of the CC chemokines macrophage inflammatory protein-1alpha and monocyte chemotactic protein-1," J. Neuroimmunol., 92, 98-108 (1998).
Kim, et al., "Expression of monocyte chemoattractant protein-1 and macrophage inflammatory protein-1 after focal cerebral ischemia in the rat," J. Neuroimmunol., 56, 127-134 (1995).
Koch, et al., "Enhanced production of monocyte chemoattractant protein-1 in rheumatoid arthritis," J. Clin. Invest., 90, 772-779 (1992).
Kohnen et al., "Patterns of inflammation in prostatic hyperplasia: a histologic and bacteriologic study," J Urology 121:755-760 (1979).
Kurihara, et al., "Defects in macrophage recruitment and host defense in mice lacking the CCR2 chemokine receptor," J. Exp. Med., 186, 1757-1762 (1997).
Kuziel, et al., "Severe reduction in leukocyte adhesion and monocyte extravasation in mice deficient in CC chemokine receptor 2," Proc. Natl. Acad. Sci. USA , 94, 12053-12058 (1997).
Labaer et al., "So, You Want to Look for Biomarkers," J Proteome Res., 4:1053-1059 (2005).
Lloyd, et al., "RANTES and monocyte chemoattractant protein-1 (MCP-1) play an important role in the inflammatory phase of crescentic nephritis, but only MCP-1 is involved in crescent formation and interstitial fibrosis," J. Exp. Med., 185, 1371-1380 (1997).
Lu, et al., "Abnormalities in monocyte recruitment and cytokine expression in monocyte chemoattractant protein 1-deficient mice," J. Exp. Med.,187, 601-608, (1998).
Lukacs, et al., "Differential recruitment of leukocyte populations and alteration of airway hyperreactivity by C-C family chemokines in allergic airway inflammation," J. Immunol., 158, 4398-4404 (1997).
Luster, "Chemokines—chemotactic cytokines that mediate inflammation," New Eng. J. Med., 338, 436-445 (1998).
Meares et al., "Bacteriologic localization patterns in bacterial prostatitis and urethritis," Invest Urol, 5,492-516 (1968).
Mirzadegan et al., "Identification of the binding site for a novel class of CCR2b chemokine receptor antagonists: binding to a common chemokine receptor motif within the helical bundle," J Biol Chem, 275:25562-25571 (2000).
Moreland et al., "Treatment of Rheumatoid Arthritis with a Recombinant Human Tumor Necrosis Factor Receptor (p75)-Fc Fusion Protein," N Engl J. Med, 337(3):141-147 (1997).
Mosmann, "T lymphocyte subsets, cytokines, and effector functions," Ann NY Acad Sci., 664:89-92 (1992).
Nadler, "IL-1β and TNF-α in Prostatic Secretions are Indicators in the Evaluation of Men with Chronic Prostatitis," Journal of Urology, 164: 214-218 (2000).
Nadler, R.B., et al., "IL-lbeta and TNF-alpha in prostatic secretions are indicators in the evaluation of men with chronic prostatitis," The Journal of Urology, (Jul. 2000) 164(1):218-8.
Neote, et al., "Molecular cloning, functional expression, and signaling characteristics of a C-C chemokine receptor" Cell, 72, 415-425 (1993).
Ni, et al. "New anti-monocyte chemoattractant protein-1 gene therapy attenuates atherosclerosis in apolipoprotein E-knockout mice," Circulation, 103, 2096-2101 (2001).
Ogata, et al. "The role of monocyte chemoattractant protein-1 (MCP-1) in the pathogenesis of collagen-induced arthritis in rats," J. Pathol., 182, 106-114 (1997).
Penna et al., 2007, "Seminal plasma cytokines and chemokines in prostate inflammation: interleukin 8 as a predicteve biomarker in chronic prostatitis/chronic pelvic pain syndrome and benign prostatic hyperplasia," European Urology, 51:524-533.
Pontari, M., et al., "Mechanisms if Prostatitis/Chronic Pelvic Pain Syndrome," (2004), The Journal of Urology, 172:839-845.
Premack and Schall, "Chemokine receptors: gateways to inflammation and infection," Nature Medicine 1996, 2, 1174-1178.
Reinecker, et al., "Monocyte-chemoattractant protein 1 gene expression in intestinal epithelial cells and inflammatory bowel disease mucosa," Gastroenterology , 108, 40-50 (1995).
Reynaud-Gaubert, et al., "Upregulation of chemokines in bronchoalveolar lavage fluid as a predictive marker of post-transplant airway obliteration," J. Heart and Lung Transplant., 21, 721-730 (2002).

Rezaie-Majd, et al, "Simvastatin reduces expression of cytokines interleukin-6, interleukin-8, and monocyte chemoattractant protein-1 in circulating monocytes from hypercholesterolemic patients," Arterioscler. Thromb. Vasc. Biol., 22, 1194-1199 (2002).

Rollins, "Chemokines," Blood, 90, 909-928 (1997).

Roque, et al. "CCR2 deficiency decreases intimal hyperplasia after arterial injury," Arterioscler. Thromb. Vasc. Biol., 22, 554-559, (2002).

Rudick et al., "Experimental autoimmune prostatitis induces chronic pelvic pain," Am J Physiol Regul Integr Comp Physiol, 294(4), R1268-1275 (2008).

Russell, et al. "Early and persistent induction of monocyte chemoattractant protein 1 in rat cardiac allografts," Proc. Natl. Acad. Sci. USA, 90, 6086-6090 (1993).

Salcedo, et al., "Human endothelial cells express CCR2 and respond to MCP-1: direct role of MCP-1 in angiogenesis and tumor progression," Blood, 96, 34-40 (2000).

Samson, et al., "Molecular cloning and functional expression of a new human CC-chemokine receptor gene," Biochemistry, 35, 3362-3367 (1996).

Saunders and Tarby, "Opportunities for novel therapeutic agents acting at chemokine receptors," Drug Disc. Today, 4, 80-92 (1999).

Schimmer, et al., "Streptococcal cell wall-induced arthritis: requirements for IL-4, IL-10, IFN-gamma, and monocyte chemoattractant protein-1," J. Immunol., 160, 1466-1471 (1998).

Schweickart, et al., "CCR11 is a functional receptor for the monocyte chemoattractant protein family of chemokines," J. Biol. Chem., 275, 9550-9556 (2000).

Smith, et al., "Contrasting genetic influence of CCR2 and CCR5 variants on HIV-1 infection and disease progression. Hemophilia Growth and Development Study (HGDS), Multicenter AIDS Cohort Study (MACS), Multicenter Hemophilia Cohort Study (MHCS), San Francisco City Cohort (SFCC), ALIVE Study.," Science, 277, 959-965, 1997.

Steiner et al., "Phenotype and function of peripheral and prostatic lymphocytes in patients with benign prostatic hyperplasia," J Urology 151:480-484 (1994).

Stern et al., "Evaluation of the cytokines macrophage inflammatory protein-1 A and monocyte chemoattractant protein-1 as indicators of inflammation in prostatic secretions," Journal of Urology (Apr. 2003) vol. 169, No. 4 Supplement, pp. 27-28. Meeting info: 98th Annual Meeting of the American Urological Association (AUA), Chicago, IL USA.

Stillwell et al., "The clinical spectrum of granulomatous prostatitis: a report of 200 cases," J Urology, 138, 320-323 (1987).

Tesch, et al., "Monocyte chemoattractant protein 1-dependent leukocytic infiltrates are responsible for autoimmune disease in MRL-Fas(Ipr) mice," J. Exp. Med., 190, 1813-1824 (1999).

Tesch, et al., "Monocyte chemoattractant protein-1 promotes macrophage-mediated tubular injury, but not glomerular injury, in nephrotoxic serum nephritis," J. Clin. Invest, 103, 73-80 (1999).

Theyer et al., "Phenotypic characterization of infiltrating leukocytes in benign prostatic hyperplasia," Lab Invest. 66, 96-107 (1992).

Trivedi et al., "Chemokines: Targets for Novel Therapeutics," Section IV, Chapter 17, Ann Reports Med Chem, 35:191-200 (2000).

Weidner et al., "Chronic Prostatitis: A Thorough Search for Etiologically Involved Microorganisms in 1,461 Patients," Infection 19:S119 (1991).

Youssef, et al., "C-C chemokine-encoding DNA vaccines enhance breakdown of tolerance to their gene products and treat ongoing adjuvant arthritis," J. Clin. Invest., 106, 361-371 (2000).

Zisman et al., "Autoantibodies to prostate specific antigen in patients with benign prostatic hyperplasia," J Urology, 154:1052-1055 (1995).

Zlotnik and Oshie, "Chemokines: a new classification system and their role in immunity," Immunity, 12, 121-127 (2000).

MCP:
IIIa vs. Control: p=0.0076
IIIb vs. Control: p=0.071
IIIa/b vs. Control: p=0.023
IIIa vs. IIIb: p=0.144

MIP:
IIIa vs. Control: p=0.165
IIIb vs. Control: p=0.186
IIIa/b vs. Control: p=0.146
IIIa vs. IIIb: p=0.864 ln(MCP):
IIIa vs. Control: p<0.0001
IIIb vs. Control: p=0.002
IIIa/b vs. Control: p=0.0002
IIIa vs. IIIb: p=0.0503 ln(MIP):
IIIa vs. Control: p<0.0001
IIIb vs. Control: p=0.0038
IIIa/b vs. Control: p=0.0003
IIIa vs. IIIb: p=0.043

| Test | Disease | | Total |
|---|---|---|---|
| | IIIa | IIIb | |
| IIIa | 47 | 2 | 59 |
| IIIb | 6 | 8 | 14 |
| Total | 53 | 10 | 73 |

Sensitivity= 70%;
Specificity= 72.7%;

(Area under ROC curve=0.748)

METHODS FOR TREATING CHRONIC PELVIC PAIN SYNDROME WITH ANTIBODIES THAT BINDS MCP-1 OR MIP-1A

This application is a continuation-in-part of allowed U.S. patent application Ser. No. 11/115,747, filed Apr. 27, 2005, which claims the benefit of U.S. Provisional Application No. 60/565,768, filed on Apr. 27, 2004, each of which is incorporated by reference in its entirety.

This invention was made with government support under Grant No. U01 DK065277-05 awarded by the National Institutes of Health (NIDD). The government has certain rights in the invention.

FIELD OF THE INVENTION

The present invention provides methods and compositions for treating chronic pelvic pain syndrome. In particular, the present invention provides methods and compositions for treating chronic pelvic pain syndrome with an agent that targets MCP-1, MIP-1α, or the CCR-2 receptor.

BACKGROUND OF THE INVENTION

Chronic prostatitis/chronic pelvic pain syndrome (collectively referred to herein as CPPS) is a syndrome of undetermined etiology occurring in men. CPPS is the third of four subgroups of prostatitis recognized by the National Institutes of Health. Category I encompasses acute bacterial prostatitis, and Category II covers chronic bacterial infection. Category III, CPPS, includes all remaining prostatitis syndromes, and is subdivided into 111a (inflammatory) and Mb (non-inflammatory). These sub-categories can be distinguished by the presence of leukocytosis in expressed prostatic secretions or sediment in a post-massage urine sample. Category IV represents asymptomatic prostatitis, which often is associated with benign prostate hyperplasia.

Prostatitis is extraordinarily common, resulting in approximately 2 million office visits to primary care physicians and urologists in the United States annually (1997 American Urological Association Annual Meeting, National Ambulatory Medical Care Survey, National Center for Health Statistics, 1990 to 1994). Patients with CPPS suffer from chronic, episodic pain in the perineum or pelvic region, irritative and obstructive voiding symptoms, and adverse effects upon sexual function (Alexander et al., Urology 48:568-574 (1996)). Men with chronic prostatitis often require repeated physician visits. Medical expenditures relating to CPPD are conservatively estimated to exceed half a billion dollars annually.

Bacterial vs. Non-Bacterial Prostatitis

Given its apparent prevalence, CPPS has defied characterization to an almost astonishing extent. While an enormous number of patients seek the care of a physician because of prostatitis-like symptoms, almost nothing is known about diagnostic criteria, etiology, or objective signs for CPPS. Pain in the pelvic region is the most frequently reported and the most severe symptom in patients with CPPS (Alexander et al., Urology 48:568-74 (1996)). It was because of these observations and the paucity of objective criteria for defining the disease, that the National Institute of Diabetes and Digestive and Kidney Diseases working group in prostatitis suggested that the disease be named Chronic Pelvic Pain Syndrome.

One reason for the present state of confusion regarding CPPS is the similarity of CPPS symptoms to the symptoms of bacterial prostatitis. Only about 5 to 10% of patients whose symptoms are consistent with bacterial prostatitis are shown to have infection in the prostate gland (Weidner et al., Infection 19:S109-S190 (1991)). The misdiagnosis of CPPS as infectious prostatitis commonly results in unnecessary treatment with multiple courses of antibiotics at burdensome costs to patients and to the health care system with no demonstrated benefit to patients.

Much effort has been expended to identify an organism underlying the cause of CPPS but no clear consensus has emerged identifying any such organism as the causative agent. Additionally, some men with CPPS have evidence of inflammation of the prostate. While the cellular and cytokine mediators involved in the inflammatory process have been increasingly clarified in the immunologic literature, few studies have investigated the immunobiology of the prostate gland to determine whether CPPS might arise from an auto-immune-like condition.

To date, diagnosis of CPPS has been based on the patient's symptoms because there are no clinical or laboratory diagnostic tests. Thus, a major need exists for an objective means for diagnosing CPPS. Specifically, what is needed are compositions and/or methods for identifying, monitoring and assessing CPPS.

SUMMARY OF THE INVENTION

The present invention provides methods and compositions for treating chronic pelvic pain syndrome. In particular, the present invention provides methods and compositions for treating chronic pelvic pain syndrome with an agent that targets MCP-1, MIP-1α, or the CCR-2 receptor. The present invention also provides biomarkers of chronic pelvic pain syndrome for use in diagnosis, drug screening, therapy monitoring, research and therapeutic applications. In particular, the present invention provides MCP-1 and MIP-1α as biomarkers of chronic pelvic pain syndrome.

In certain embodiments, the present invention provides methods of treating a subject having, or suspected of having, chronic pelvic pain syndrome comprising: treating a subject with an agent that targets MCP-1, MIP-1α, or the CCR-2 receptor, wherein the subject has one or more symptoms of chronic pelvic pain syndrome, and wherein the treating is under conditions such that at least one of the symptoms is reduced or eliminated.

In additional embodiments, the agent comprises an anti-MCP-1 monoclonal antibody or an anti-MIP-1α monoclonal antibody. In further embodiments, the agent comprises polyclonal antibodies directed towards MCP-1 or MIP-1α. In further embodiments, the agent comprises siRNA oligonucleotides, miRNA oligonucleotides, or antisense oligonucleotides. In further embodiments, the agent is selected from the group consisting of: an indolopiperidine, a spiropiperidine, a 2-substituted indole, a pyrazolone derivative, a 2-substituted benzimidazole, an N,N-dialkylhomopiperazine, a bicyclic pyrrole, a 5-aryl pentadienamide, a cyclic amine derivative, MCP-1(9-76), a compound selected from compounds 1-2209 from WO99/25686.

In some embodiments, the present invention provides methods of diagnosing and treating chronic pelvic pain syndrome comprising: a) detecting the expression of MCP-1 and/or MIP-1α in the sample from a subject, wherein the subject has one or more symptoms of chronic pelvic pain syndrome; and b) treating the subject with an agent that targets MCP-1, MIP-1α, the CCR-2 receptor, wherein the treating is under conditions such that at least one of the symptoms is reduced or eliminated.

In certain embodiments, the chronic pelvic pain syndrome is non-inflammatory chronic pelvic pain syndrome. In further embodiments, the subject is male, and wherein the sample comprises an expressed prostatic secretion sample from the subject. In further embodiments, the expressed prostatic secretion sample comprises less than 10 white blood cells per 400× high power field. In additional embodiments, the detecting comprising detecting an elevated level of expression of an MCP-1 polypeptide and/or an MIP-1α polypeptide in the sample. In further embodiments, the subject is a human subject. In additional embodiments, the detecting the expression of MCP-1 and/or MIP-1α comprises detecting the presence of MCP-1 and/or MIP-1α mRNA. In other embodiments, the sample comprises semen, seminal fluid, and/or expressed prostatic secretions. In some embodiments, the agent is selected from the group consisting of: an indolopiperidine, a spiropiperidine, a 2-substituted indole, a pyrazolone derivative, a 2-substituted benzimidazole, an N,N-dialkylhomopiperazine, a bicyclic pyrrole, a 5-aryl pentadienamide, a cyclic amine derivative, MCP-1(9-76), a compound selected from compounds 1-2209 from WO99/25686. In certain embodiments, the agent comprises an anti-MCP-1 monoclonal antibody or an anti-MIP-1α monoclonal antibody. In other embodiments, the agent comprises siRNA oligonucleotides, miRNA oligonucleotides, or antisense oligonucleotides.

In particular embodiments, the present invention provides methods of treating chronic pelvic pain syndrome comprising: a) providing a male subject with one or more symptoms of chronic pelvic pain syndrome, wherein the subject is known to express elevated levels of MCP-1 and/or MIP-1α in their semen, seminal fluid, or prostatic secretions; and b) treating the subject with an agent that targets MCP-1, MIP-1α, the CCR-2 receptor, wherein the treating is under conditions such that at least one of the symptoms is reduced or eliminated.

In some embodiments, the present invention provides a method for detecting chronic pelvic pain syndrome in a subject, comprising providing a sample from a subject; and detecting the expression of MCP-1 and/or MIP-1α in the sample. In some embodiments, detecting the expression of MCP-1 and/or MIP-1α comprises detecting the presence of MCP-1 and/or MIP-1α mRNA. In some embodiments, detecting expression of MCP-1 and/or MIP-1α mRNA comprises exposing the MCP-1 and/or MIP-1α mRNA to a nucleic acid probe complementary to the MCP-1 and/or MIP-1α mRNA. In some embodiments, detecting expression of MCP-1 and/or MIP-1α comprises detecting the presence of a MCP-1 and/or MIP-1α polypeptide. In some embodiments, detecting the presence of a MCP-1 and/or MIP-1α polypeptide comprises exposing the MCP-1 and/or MIP-1α polypeptide to an antibody specific to the MCP-1 and/or MIP-1α polypeptide and detecting the binding of the antibody to the MCP-1 and/or MIP-1α polypeptide. In some embodiments, the subject comprises a human subject. In some embodiments, the sample comprises semen, seminal fluid, and/or expressed prostatic secretions.

The present invention also provides a method for selecting a therapeutic course of action, comprising providing a sample from a subject; detecting the expression of MCP-1 and/or MIP-1α in the sample; and treating the subject based upon the expression of MCP-1 and/or MIP-1α.

The present invention provides a kit for characterizing CPPS in a subject, comprising a reagent capable of specifically detecting the presence or absence of expression of MIP-1α and/or MCP-1; and instructions for using the kit for characterizing cancer in the subject. In some embodiments, the reagent comprises a nucleic acid probe complementary to a MIP-1α and/or MCP-1 mRNA. In some embodiments, the reagent comprises an antibody that specifically binds to a MIP-1α and/or MCP-1 polypeptide.

The present invention also provides a method of screening compounds, comprising providing a sample; and one or more test compounds; and contacting the sample with the test compound; and detecting a change in MIP-1α and/or MCP-1 expression in the sample in the presence of the test compound relative to the absence of the test compound. In some embodiments, the detecting comprises detecting MIP-1α and/or MCP-1 mRNA. In some embodiments, the detecting comprises detecting MIP-1α and/or MCP-1 polypeptide. In some embodiments, the cell is in vitro or in vivo. In some embodiments, the test compound comprises an antisense compound. In some embodiments, the test compound comprises a drug.

DEFINITIONS

Figure 1A:
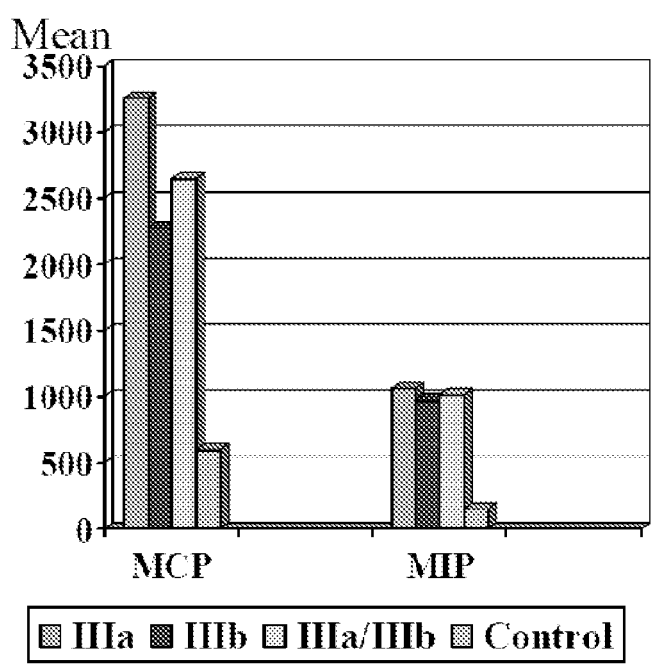
FIG. 1A shows a comparison of levels of MIP-1α and MCP-1 in subjects with CPPS types Ma and Mb compared to controls and FIG. 1B shows a comparison of levels of MIP-1α and MCP-1 in subjects with CPPS types Ma and Mb compared to controls on a Log Scale.

To facilitate an understanding of the present invention, a number of terms and phrases are defined below:

The term "epitope" as used herein refers to that portion of an antigen that makes contact with a particular antibody.

As used herein, the term "subject" refers to any animal (e.g., a mammal), including, but not limited to, humans, non-human primates, rodents, and the like, which is to be the recipient of a particular treatment or subject to various tests (e.g., diagnostic tests) that may be provided by the present invention. Typically, the terms "subject" and "patient" are used interchangeably herein in reference to a human subject.

As used herein, the term "subject suspected of having CPPS" refers to a subject that presents one or more symptoms indicative of chronic pelvic pain syndrome (CPPS) or is being screened for CPPS (e.g., during a routine physical). A subject suspected of having CPPS may also have one or more risk factors. A subject suspected of having CPPS has generally not been tested for CPPS. However, a "subject suspected of having CPPS" encompasses an individual who has received an initial diagnosis but for whom the nature of the CPPS is not known. The term further includes people who once had CPPS.

As used herein, the term "subject at risk for CPPS" refers to a subject with one or more risk factors for developing CPPS.

As used herein, the term "characterizing CPPS in a subject" refers to the identification of one or more properties of CPPS in a subject.

The terms "test compound" and "candidate compound" refer to any chemical entity, pharmaceutical, drug, and the like that is a candidate for use to treat or prevent a disease, illness, sickness, or disorder of bodily function (e.g., CPPS). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include, among other things, body fluids (e.g., semen), blood products (e.g., plasma, serum and the like), and their component parts (e.g., expressed prostatic secretions, termed "ESPs" herein, seminal plasma or seminal fluid). Environmental samples include environmental material such as surface matter, soil, water, and industrial samples. Such examples are not however to be construed as limiting the sample types applicable to the present invention.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "CPPS marker" or "CPPS marker genes" refers to a gene whose expression level (e.g., as detected by mRNA or protein expression), alone or in combination with other genes, is correlated with CPPS or prognosis of CPPS. The correlation may relate to either an increased or decreased expression of the gene. For example, the expression of the gene may be indicative of CPPS, or reduced level of expression of the gene may be correlated with response to therapy for CPPS in a CPPS patient. CPPS marker expression may be characterized using any suitable method, including but not limited to, those described in Examples 1 through 3 below.

As used herein, the term "a reagent that specifically detects expression levels" refers to reagents used to detect the expression of one or more genes (e.g., including but not limited to, the CPPS markers of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-CPPS control" refers to measuring the level of expression of a gene (e.g., the level of mRNA or protein) relative to the level in a non-CPPS control sample. Gene expression can be measured using any suitable method, including but not limited to, those described herein.

As used herein, the term "detecting a change in gene expression (e.g., MCP and MIP) in a sample in the presence of said test compound relative to the absence of said test compound" refers to measuring an altered level of expression (e.g., increased or decreased) in the presence of a test compound relative to the absence of the test compound. Gene expression can be measured using any suitable method, including but not limited to, those described in Examples 1-3 below.

As used herein, the term "instructions for using said kit for detecting CPPS in said subject" includes instructions for using the reagents contained in the kit for the detection and characterization of CPPS in a sample from a subject.

As used herein, the term "CPPS expression profile map" refers to a presentation of expression levels of genes in a sample (e.g., prostate tissue or seminal fluid) The map may be presented as a graphical representation (e.g., on paper or on a computer screen), a physical representation (e.g., a gel or array) or a digital representation stored in computer memory. Each map corresponds to a particular type of sample and thus provides a template for comparison to a patient sample. In preferred embodiments, maps are generated from pooled samples comprising samples from a plurality of patients with the same type of sample.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "providing a prognosis" refers to providing information regarding the impact of the presence of CPPS (e.g., as determined by the diagnostic methods of the present invention) on a subject's future health (e.g., likelihood of responding to therapy).

As used herein, the term "subject diagnosed with a CPPS" refers to a subject who has been tested and found to have CPPS. The CPPS may be diagnosed using any suitable method, including but not limited to, the diagnostic methods of the present invention.

As used herein, the term "initial diagnosis" refers to results of initial CPPS diagnosis (e.g. the presence or absence of CPPS).

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer".

Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharamcia), 5 g BSA (Fraction V; Sigma)) and 100 gg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 (1972)). Other nucleic acids will not be replicated by this amplification enzyme. Similarly, in the case of T7 RNA polymerase, this amplification enzyme has a stringent specificity for its own promoters (Chamberlin et al., Nature 228:227 (1970)). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 (1989)). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989)).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 (1989)).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 (1989)).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973)), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene that is used in conjunction with CAD-deficient cells and the mammalian hypoxanthine-guanine phosphoribosyl transferase (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., CPPS). Test compounds comprise both known and potential therapeutic compounds. A test compound can be determined to be therapeutic by screening using the screening methods of the present invention. In some embodiments of the present invention, test compounds include antisense compounds.

DETAILED DESCRIPTION OF THE INVENTION

The present invention provides methods and compositions for treating chronic pelvic pain syndrome. In particular, the present invention provides methods and compositions for treating chronic pelvic pain syndrome with an agent that targets MCP-1, MIP-1α, or the CCR-2 receptor.

There is a substantial body of evidence that demonstrates the occurrence of immunological activity within the prostate gland. However, the nature and cause of this activity, and whether it is detrimental to the host, has not been determined. Inflammatory infiltrates in the prostate are very common. In one study of 162 cases of surgically resected prostatic tissue, 98% possessed inflammatory infiltrates (Kohnen et al., J. Urology 121:755-60 (1979)). The infiltrating cells consisted of monocytes and activated T and B lymphocytes (Theyer et al., Lab Invest. 66:96-107 (1992); Steiner et al., J. Urology 151:480-84 (1994)).

A rare form of prostatic inflammation, granulomatous prostatitis, has been characterized, although the etiology of the inflammation is also unknown. One major theory about the disease, however, is that it represents an immune reaction against self prostatic proteins induced by infection or manipulation of the gland by previous biopsy or surgical procedure (Stillwell et al., J. Urology 138:320-23 (1987); Dhundee et al., Histopathology 18:435-41 (1991)).

The disease is also observed after instillation of Bacillus Calmette-Guerin (BCG) into the bladder as a treatment for superficial bladder cancer (Bahnson, J. Urology 146:1368-69 (1991)).

Recent observations about the existence of subsets of CD4+ T cells has yielded fundamental information about immune responses in humans. CD4+ T cells can be separated into subsets based upon the patterns of cytokines they secrete (Mosmann, Ann NY Acad. Sci. 664:89-92 (1992)). CD4+ T cells that secrete, among other cytokines, IFN-γ and IL-2 are called T helper 1 (Th1) cells. Th1 cells mediate cellular immunity, such as delayed hypersensitivity responses. CD4+ T cells that secrete, among other cytokines, IL-4 and IL-10 are termed T helper 2 (Th2). Th2 cells are associated with antibody production and allergy. Immune responses mediated by Th1 and Th2 cells can be characterized by the local cytokine environment during an immune response.

Zisman et al. found IgG anti-PSA antibody titers to be higher in the serum of men with benign prostate hyperplasia (BPH) compared to controls (Zisman et al., J. Urology 154: 1052-55 (1995)). However, of 17 men with chronic prostatitis, no discernable difference was found in mean antibody titer as compared to controls. Zisman et al. speculate that an immunologic mechanism may play a role in the symptomatology of BPH. An alternative explanation is that a Th1 type of response may be occurring in patients with chronic prostatitis/chronic pelvic pain syndrome. In this event, no antibody response would be expected.

Nonbacterial prostatitis, recently defined as chronic pelvic pain syndrome (CPPS), is characterized by pelvic or perineal pain and is associated with prostatic inflammation (Chronic Prostatitis Workshop, National Institute of Health, Bethesda, Md., Dec. 7-8, 1995). CPPS is the most common urologic diagnosis in men less than 50 years of age, yet little is known about its etiology and treatment. Nonbacterial prostatitis has been traditionally defined by the identification of white blood cells (WBC) in expressed prostatic secretions (EPS) in the absence of bacterial infection (Meares et al., Invest Urol, 5: 492 (1968)). Thus, the identification of inflammatory mediators such as cytokines in EPS are contemplated to be useful in the classification of men with CPPS.

Cytokines are small protein molecules produced and used by immune and inflammatory cells to communicate, control the environment, and regulate local and systemic events of the immune response. Most cytokines are produced and released locally and mediate their effects at the site of injury, infection or inflammation by autocrine and paracrine mechanisms. A number of cytokines regulate inflammation, including interleukin-1 (IL-1) and tumor necrosis factor alpha (TNF-α). IL-1α and IL-1β, collectively termed IL-1, share only 26% homology but act via the same high affinity receptor (Dower et al., J Exp Med, 162: 501 (1985)). IL-1 has a wide range of target cells and acts to promote antigen specific immune responses, inflammation and tissue repair. TNF-α is synthesized by cells of the monocyte/macrophage lineage. Synthesis of TNF-α is induced by bacterial proteins, viruses and fungal antigens, making its role in infection and inflammation prominent. To better understand the nature of CPPS, the inventors evaluated the EPS of men with no urologic disease, Benign Prostatic Hyperplasia (BPH), CPPS and asymptomatic inflammatory prostatitis (AIP) for the presence of leukocytes and cytokines.

Previous studies by the inventors demonstrated that the cytokines interleukin-1 (IL-1), tumor necrosis factor-α (TNF-α), IL-8, and epithelial neutrophil activating peptide-78 were significantly higher in samples from men with IIIa, but not IIIb, CPPS compared to controls (See, e.g., Nadler et al., Journal of Urology, 164: 214-218 (2000)).

The present invention relates to compositions and methods for prostatic disease (e.g., CPPS) diagnostics, including but not limited to, CPPS markers (e.g., MIP-1α and MCP-1). In particular, the present invention provides expression profiles associated with prostatic disease. Accordingly, the present invention provides methods of characterizing samples (e.g., expressed prostatic secretions or semen), kits for the detection of markers, as well as drug screening and therapeutic applications.

I. Markers for Prostatic Disease

The present invention provides markers whose expression is specifically altered in prostatic disease. Such markers find use in the diagnosis and characterization of prostatic disease (e.g., CPPS).

A. Identification of Markers

In experiments conducted using the compositions and methods of the present invention, the inventors determined that the chemokines MIP-1α and MCP-1 are present, and significantly elevated, in samples (e.g., expressed prostatic secretions) of men with both IIIa and IIIb CPPS (See, e.g., Example 2, FIGS. 1A and B).

Thus, in some embodiments, the present invention provides biologic markers for CPPS (e.g., MIP-1α and MCP-1). In some embodiments, detecting the levels of cytokines MIP-1α and/or MCP-1 in a sample permits diagnosis of prostatic disease (e.g., CPPS). In some embodiments, biomarkers of the present invention (e.g., MIP-1α and MCP-1) are used in order to further understand and characterize the etiology and pathogenesis of CPPS.

It is contemplated that the levels of cytokines (e.g., MIP-1α and MCP-1) are detected in a sample. In some embodiments, samples are obtained from a subject (e.g., a patient), and include, but are not limited to, fluids, solids, tissues, and gases. In some embodiments, biological samples include, among other things, body fluids (e.g., semen or saliva), blood products (e.g., plasma, serum and the like), and their component parts. In preferred embodiments, samples include expressed prostatic secretions, seminal plasma and/or seminal fluid.

In some embodiments, the present invention provides detection of and/or measurement of chemokines (e.g., MIP-1α and MCP-1) as indicative of the presence or absence of prostate disease (e.g., CPPS) in a subject. In some embodiments, patients are categorized (e.g., as IIIa and IIIb) and therapies (e.g., anti-chemokine therapies) selected according to the levels of MIP-1α and MCP-1 detected. It is contemplated that, in some embodiments, subjects with certain levels of MIP-1α and MCP-1 (e.g., elevated levels, See, e.g., Example 3, FIGS. 2 and 3), as compared to controls, are classified as possessing prostatic disease (CPPS). In some embodiments, being classified as a prostatic disease patient correlates with the likelihood of responding to chemokine directed therapy (e.g. anti-MIP-1α and anti-MCP-1 treatment).

In some embodiments, chemokines (e.g., MIP-1α and MCP-1) are detected individually. In some embodiments, chemokines (e.g., MIP-1α and MCP-1) are detected together. It is contemplated that, according to experiments conducted during the development of the present invention (See, e.g., Examples 2-3), that detection of both MIP-1α and MCP-1 enhances the sensitivity of predicting disease (e.g., prostatic) and classifying disease (e.g., CPPS) over the use of either individually. In some embodiments, detection of MIP-1α and/or MCP-1, is used in combination with detection of other chemokines/cytokines, including, but not limited to GMCSF, IL-1, IL-2, IL-3, IL-4, IL-5, IL-6, IL-7, IL-8, IL-9, IL-10, IL-11, IL-12, IL-13, IL-14, IL-15, β-inteferon, γ-interferon, GRO-α, RENTES, fractalkine, VEGF, and TNF, in order to detect or classify disease (e.g., CPPS and CPSI, respectively).

B. Detection of Markers

In some embodiments, the present invention provides methods for detection of expression of prostatic disease (e.g., CPPS markers). In preferred embodiments, expression is measured directly (e.g., at the RNA or protein level). In some embodiments, expression is detected in samples (e.g., semen, seminal fluid, seminal plasma or expressed prostatic secretions). In other embodiments, expression is detected in bodily fluids (e.g., including but not limited to, plasma, serum, whole blood, mucus, and urine). The present invention further provides panels and kits for the detection of markers. In preferred embodiments, the presence of a CPPS marker is used to provide a prognosis to a subject. For example, the detection of MIP-1α and/or MCP-1 in samples is indicative of CPPS. The information provided is also used to direct the course of treatment. For example, if a subject is found to have a marker (e.g., as described herein) indicative of the presence of CPPS, therapies (e.g., anti-MIP-1α and anti-MCP-1 agents) can be started immediately in place of or in addition to antibiotic treatment. In addition, if a subject is found to have a CPPS that is not responsive to antibiotic therapy, the expense and inconvenience of such therapies can be avoided.

The present invention is not limited to the markers described above. Any suitable marker that correlates with CPPS may be utilized, including but not limited to, GMCSF, IL-1, IL-2, IL-3, IL-4, IL-5, IL-6, IL-7, IL-8, IL-9, IL-10, IL-11, IL-12, IL-13, IL-14, IL-15,β-inteferon, γ-interferon, GRO-α, RENTES, fractalkine, VEGF, and TNF. Additional markers are also contemplated to be within the scope of the present invention. Any suitable method may be utilized to identify and characterize markers suitable for use in the methods of the present invention, including but not limited to, those described in illustrative Examples 1-3 below. For example, in some embodiments, markers identified as being up or down-regulated in CPPS using the gene expression microarray methods of the present invention are further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers. The panel allows for the simultaneous analysis of multiple markers correlating with CPPS. For example, a panel may include markers identified as correlating with CPPS Categories I-IV. Depending on the subject, panels may be analyzed alone or in combination in order to provide the best possible diagnosis and prognosis. Markers for inclusion on a panel are selected by screening for their predictive value using any suitable method, including but not limited to, those described in the illustrative examples below.

In other embodiments, the present invention provides an expression profile map comprising expression profiles of CPPS. Such maps can be used for comparison with patient samples. Comparisons can be made utilizing any suitable method, including but not limited to, computer comparison of digitized data. The comparison data is used to provide diagnoses and/or prognoses to patients.

1. Detection of RNA

In some preferred embodiments, detection of CPPS markers (e.g., including but not limited to, those disclosed herein) is detected by measuring the expression of corresponding mRNA in a tissue sample (e.g., prostate tissue). mRNA expression may be measured by any suitable method, including but not limited to, those disclosed below.

In some embodiments, RNA is detection by Northern blot analysis. Northern blot analysis involves the separation of RNA and hybridization of a complementary labeled probe.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to a oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of CPPS markers is detected by measuring the expression of the corresponding protein or polypeptide. Protein expression may be detected by any suitable method. In some embodiments, proteins are detected by immunohistochemistry or ELISA as in Example 1 below. In some embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay, Examples 1-3), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to CPPS markers is utilized.

In other embodiments, the immunoassay described in U.S. Pat. Nos. 5,599,677 and 5,672,480; each of which is herein incorporated by reference.

3. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a semen, serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine or semen sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., Category III CPPS) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition associated with the disease.

4. Kits

In yet other embodiments, the present invention provides kits for the detection and characterization of prostatic disease. In some embodiments, the kits contain antibodies specific for a CPPS marker, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

5. In Vivo Imaging

In some embodiments, in vivo imaging techniques are used to visualize the expression of CPPS markers in an animal (e.g., a human or non-human mammal). For example, in some embodiments, CPPS marker mRNA or protein is labeled using an labeled antibody specific for the CPPS marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the CPPS markers of the present invention are described below.

The in vivo imaging methods of the present invention are useful in the diagnosis of CPPS that express the CPPS markers of the present invention (e.g., Category IIIa and IIIb). In vivo imaging is used to visualize the presence of a marker indicative of CPPS. Such techniques allow for diagnosis without the use of an unpleasant biopsy. The in vivo imaging methods of the present invention are also useful for providing prognoses to patients suffering from CPPS. For example, the presence of a marker indicative of CPPS likely to respond to treatment can be detected. The in vivo imaging methods of the present invention can further be used to detect MIP-1α and MCP-1 involved in inflammatory processes in other parts of the body.

In some embodiments, reagents (e.g., antibodies) specific for the CPPS markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 (1990) have described an optimized antibody-chelator for the radioimmunoscintographic imaging of tumors using Indium-111 as the label. Griffin et al., (J Clin One 9:631-640 (1991)) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 (1991)). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 (1980)) for In-111 and Tc-99m, and by Scheinberg et al. (Science 215:1511 (1982)). Other chelating agents may also be used, but the 1-(p-carboxymethoxybenzyl) EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 (1982)) for labeling of albumin with In-111, but which can be adapted for labeling of antibodies. A suitable method of labeling antibodies with Tc-99m which does not use chelation with DPTA is the pre-tinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 (1978)) for plasma protein, and recently applied successfully by Wong et al. (J. Nucl. Med., 23:229 (1981)) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific CPPS marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a CPPS marker of the present invention). When active, it leads to a reaction that emits light. A CCD camera and software is used to capture the image and analyze it.

II. Antibodies

To the extent that antibodies to MIP-1α and MCP-1 are not readily available (e.g., are not commercially available), or optimization of existing antibodies is desired, the present invention provides isolated antibodies. In preferred embodiments, the present invention provides monoclonal antibodies that specifically bind to an isolated polypeptide comprised of at least five amino acid residues of the CPPS markers described herein (e.g., MIP-1α and MCP-1). These antibodies find use in the diagnostic methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 (1975)). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against MIP-1α and MCP-1 of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a CPPS marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a CPPS marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

III. Drug Screening

In some embodiments, the present invention provides drug screening assays (e.g., to screen for CPPS drugs). The screening methods of the present invention utilize CPPS markers identified using the methods of the present invention (e.g., including but not limited to, MIP-1α and MCP-1). For example, in some embodiments, the present invention provides methods of screening for compound that alter (e.g., increase or decrease) the expression of CPPS marker genes. In some embodiments, candidate compounds are antisense agents (e.g., oligonucleotides) directed against CPPS markers. See Section IV below for a discussion of antisense therapy. In other embodiments, candidate compounds are antibodies that specifically bind to a CPPS marker of the present invention.

In one screening method, candidate compounds are evaluated for their ability to alter CPPS marker expression by contacting a compound with a cell expressing a CPPS marker and then assaying for the effect of the candidate compounds on expression. In some embodiments, the effect of candidate compounds on expression of a CPPS marker gene is assayed for by detecting the level of CPPS marker mRNA expressed by the cell. mRNA expression can be detected by any suitable method. In other embodiments, the effect of candidate compounds on expression of CPPS marker genes is assayed by measuring the level of polypeptide encoded by the CPPS markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to CPPS markers of the present invention (e.g, MIP-1α and MCP-1), have an inhibitory (or stimulatory) effect on, for example, CPPS marker expression or CPPS markers activity, or have a stimulatory or inhibitory effect on, for example, the expression or activity of a CPPS marker substrate. Compounds thus identified can be used to modulate the activity of target gene products (e.g., CPPS marker genes) either directly or indirectly in a therapeutic protocol, to elaborate the biological function of the target gene product, or to identify compounds that disrupt normal target gene interactions. Compounds which inhibit the activity or expression of CPPS markers are useful in the treatment of inflammatory disorders (e.g., CPPS, rheumatoid arthritis, and Crohn's disease).

In one embodiment, the invention provides assays for screening candidate or test compounds that are substrates of a CPPS markers protein or polypeptide or a biologically active portion thereof. In another embodiment, the invention provides assays for screening candidate or test compounds that bind to or modulate the activity of a CPPS marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994).

Libraries of compounds may be presented in solution (e.g., Houghten, Biotechniques 13:412-421 (1992)), or on beads (Lam, Nature 354:82-84 (1991)), chips (Fodor, Nature 364: 555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249: 404-406 (1990); Cwirla et al., Proc. Natl. Acad. Sci. 87:6378-6382 (1990); Felici, J. Mol. Biol. 222:301 (1991)).

In one embodiment, an assay is a cell-based assay in which a cell that expresses a CPPS marker protein or biologically active portion thereof is contacted with a test compound, and the ability of the test compound to modulate the CPPS marker's activity is determined. Determining the ability of the test compound to modulate CPPS marker activity can be accomplished by monitoring, for example, changes in enzymatic activity. The cell, for example, can be of mammalian origin.

The ability of the test compound to modulate CPPS marker binding to a compound, e.g., a CPPS marker substrate (e.g., the MIP-1α receptor), can also be evaluated. This can be accomplished, for example, by coupling the compound, e.g., the substrate, with a radioisotope or enzymatic label such that binding of the compound, e.g., the substrate, to a CPPS marker can be determined by detecting the labeled compound, e.g., substrate, in a complex.

Alternatively, the CPPS marker is coupled with a radioisotope or enzymatic label to monitor the ability of a test compound to modulate CPPS marker binding to a CPPS markers substrate in a complex. For example, compounds (e.g., substrates) can be labeled with $^{125}I$, $^{35}S$ $^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a CPPS marker substrate) to interact with a CPPS marker with or without the labeling of any of the interactants can be evaluated. For example, a microphysiometer can be used to detect the interaction of a compound with a CPPS marker without the labeling of either the compound or the CPPS marker (McConnell et al. Science 257:1906-1912 (1992)). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and CPPS markers.

In yet another embodiment, a cell-free assay is provided in which a CPPS marker protein or biologically active portion thereof is contacted with a test compound and the ability of the test compound to bind to the CPPS marker protein or biologically active portion thereof is evaluated. Preferred biologically active portions of the CPPS marker proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the CPPS marker protein to bind to a target molecule can be accomplished using real-time Biomolecular Interaction Analysis (BIA) (see, e.g., Sjolander and Urbaniczky, Anal. Chem. 63:2338-2345 (1991) and Szabo et al. Curr. Opin. Struct. Biol. 5:699-705 (1995)). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize CPPS markers, an anti-CPPS marker antibody or its target molecule to facilitate separation of complexed from non-complexed forms of one or both of the proteins, as well as to accommodate automation of the assay. Binding of a test compound to a CPPS marker protein, or interaction of a CPPS marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-CPPS marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or CPPS marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of CPPS markers binding or activity determined using standard techniques. Other techniques for immobilizing either CPPS markers protein or a target molecule on matrices include using conjugation of biotin and streptavidin. Biotinylated CPPS marker protein or target molecules can be prepared from biotin-NHS(N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with CPPS marker protein or target molecules but which do not interfere with binding of the CPPS markers protein to its target molecule. Such antibodies can be derivatized to the wells of the plate, and unbound target or CPPS markers protein trapped in the wells by antibody conjugation. Methods for detecting such complexes, in addition to those described above for the GST-immobilized complexes, include immunodetection of complexes using antibodies reactive with the CPPS marker protein or target molecule, as well as enzyme-linked assays which rely on detecting an enzymatic activity associated with the CPPS marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 (1993)); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit. 11:141-8 (1998); Hageand Tweed J. Chromatogr. Biomed. Sci. Appl 699:499-525 (1997)). Further, fluorescence energy transfer may also be conveniently utilized, as described herein, to detect binding without further purification of the complex from solution.

The assay can include contacting the CPPS markers protein or biologically active portion thereof with a known compound that binds the CPPS marker to form an assay mixture, contacting the assay mixture with a test compound, and determining the ability of the test compound to interact with a CPPS marker protein, wherein determining the ability of the test compound to interact with a CPPS marker protein includes determining the ability of the test compound to preferentially bind to CPPS markers or biologically active portion thereof, or to modulate the activity of a target molecule, as compared to the known compound.

To the extent that CPPS markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, CPPS marker proteins can be used as a "bait protein" in a two-hybrid assay or three-hybrid assay (see, e.g., U.S. Pat. No. 5,283,317; Zervos et al., Cell 72:223-232 (1993); Madura et al., J. Biol. Chem. 268.12046-12054 (1993); Bartel et al., Biotechniques 14:920-924 (1993); Iwabuchi et al., Oncogene 8:1693-1696 (1993); and Brent WO 94/10300; each of which is herein incorporated by reference), to identify other proteins, that bind to or interact with CPPS markers ("CPPS marker-binding proteins" or "CPPS marker-bp") and are involved in CPPS marker activity. Such CPPS marker-bps can be activators or inhibitors of signals by the CPPS marker proteins or targets as, for example, downstream elements of a CPPS markers-mediated signaling pathway.

Modulators of CPPS markers expression can also be identified. For example, a cell or cell free mixture is contacted with a candidate compound and the expression of CPPS marker mRNA or protein evaluated relative to the level of expression of CPPS marker mRNA or protein in the absence of the candidate compound. When expression of CPPS marker mRNA or protein is greater in the presence of the candidate compound than in its absence, the candidate compound is identified as a stimulator of CPPS marker mRNA or protein expression. Alternatively, when expression of CPPS marker mRNA or protein is less (i.e., statistically significantly less) in the presence of the candidate compound than in its absence, the candidate compound is identified as an inhibitor of CPPS marker mRNA or protein expression. The level of CPPS markers mRNA or protein expression can be determined by methods described herein for detecting CPPS markers mRNA or protein.

A modulating agent can be identified using a cell-based or a cell free assay, and the ability of the agent to modulate the activity of a CPPS markers protein can be confirmed in vivo, e.g., in an animal such as an animal model for a disease (e.g., an animal of CPPS of any Category I-IV).

This invention further pertains to novel agents identified by the above-described screening assays (See e.g., below description of CPPS therapies). Accordingly, it is within the scope of this invention to further use an agent identified as described herein (e.g., a CPPS marker modulating agent, an antisense CPPS marker nucleic acid molecule, a siRNA molecule, a CPPS marker specific antibody, or a CPPS marker-binding partner) in an appropriate animal model (such as those described herein) to determine the efficacy, toxicity, side effects, or mechanism of action, of treatment with such an agent. Furthermore, novel agents identified by the above-described screening assays can be used for treatments as described herein.

IV. Prostatic Disease Therapies

In some embodiments, the present invention provides therapies for prostatic disease (e.g., CPPS). In some embodiments, therapies target CPPS markers (e.g., including but not limited to, MIP-1α and MCP-1).

A. Antisense Therapies

In some embodiments, the present invention targets the expression of CPPS markers. For example, in some embodiments, the present invention employs compositions comprising oligomeric antisense compounds (e.g., siRNA, miRNA, anti-sense oligonucleotides), particularly oligonucleotides (e.g., those identified in the drug screening methods described above), for use in modulating the function of nucleic acid molecules encoding CPPS markers of the present invention, ultimately modulating the amount of CPPS marker expressed. This is accomplished by providing antisense compounds that specifically hybridize with one or more nucleic acids encoding CPPS markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of CPPS markers of the present invention. In the context of the present invention, "modulation" means either an increase (stimulation) or a decrease (inhibition) in the expression of a gene. For example, expression may be inhibited to potentially prevent inflammation associated with CPPS.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a CPPS marker of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3))_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Hely. Chim. Acta 78:486 (1995)) i.e., an alkoxyalkoxy group. A further preferred modification includes 2'-dimethylaminooxyethoxy (i.e., a $O(CH_2)_2ON(CH_3)_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_3)_2$. Other preferred modifications include 2'-methoxy(2'-O—$CH_3$), 2'-aminopropoxy(2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-5-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisensce oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Genetic Therapies

The present invention contemplates the use of any genetic manipulation for use in modulating the expression of CPPS markers of the present invention. Examples of genetic manipulation include, but are not limited to, gene knockout (e.g., removing the CPPS marker gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Appl. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Anti-Chemokine Therapy

Compounds which interfere with the production and/or activity of various cytokines are widely known. The term "anti-cytokine compound" as used herein includes compounds which inhibit production, processing or activity of a cytokine or its receptor. Such compounds may, for example, bind to the cytokine or its receptor, thereby preventing the natural cytokine-receptor interaction.

Thus, the invention also provides a method for treating subjects determined to be suffering from CPPS or other disorders associated with elevated levels of one or more cytokines in one or more components or fractions of semen, preferably seminal plasma, comprising administering one or more anti-cytokine agents, including, but not limited to those disclosed in U.S. Pat. No. 6,180,355. In preferred embodiments of the claimed methods, the anti-cytokine agent is administered to a patient suffering from a disorder falling within the definition of CPPS, including prostatitis. In some embodiments, a combinatorial approach may be taken, in which a patient receives one or more anti-cytokine agents, or, may receive an anti-cytokine agent in addition to an antisense therapy mentioned above. It is contemplated that such a combinatorial approach may have additive, or more than additive, effects.

The anti-cytokine agent may be provided in a formulation suitable for administration to a patient. Such formulations are known in the art and depend on the chemical and physiological characteristics of the particular anti-cytokine agent.

The dosage regimen is readily determined by one of skill in the art, taking into account various factors which affect the action of the particular anti-cytokine agent. For example, dosage may vary depending on the condition, type and/or severity of damaged tissue; the patient's age and/or diet; time, mode, and/or route of administration, as well as other clinical factors known in the art. Generally, systemic or injectable administration, such as intravenous (IV), intramuscular (IM) or subcutaneous (Sub-Q) injection, will be initiated at a dose which is minimally effective. The dose will then be gradually increased until a positive effect is observed. Incremental increases should be continued, so long as such increases produce a corresponding increase in effect, while taking into account any adverse affects that may appear. The addition of any other anti-cytokine agents or other agents in general (e.g., antisense compounds) to the final composition may also affect the final dosage. Progress may be monitored by analyzing the cytokine levels by the diagnostic assay described herein.

Many anti-cytokine compounds are known and/or are under development for treatment of other conditions associated with cytokines, such as rheumatoid arthritis, insulin dependent diabetes, sepsis and Crohn's disease (See, e.g., Haworth et al., "Cytokine and Anti-Cytokine Therapy", The Cytokine Handbook, Thomson, Angus, ed., pp. 777-801 (1998)). Synthesis of cytokines can be inhibited by a variety of known agents, including phosphodiesterase inhibitors, prostanoids, adenosine, corticosteroids and IL-10. Glucocorticoids and prostaglandin $E_2$ ($PGE_2$) also inhibit cytokine synthesis. The effects of released cytokines can be antagonized by cytokine antagonists, such as soluble cytokine receptors or anti-cytokine antibodies. Ways to develop such antibodies are disclosed herein.

Anti-cytokine agents which can be used in the methods of the present invention also include various endogenous mediators, and synthetic drugs.

Endogenous mediators which can be used as anti-cytokine agents include, for example, corticosteroids, prostanoids, adenosine, histamine, nitric oxide, retinoic acid, and n-3 polyunsaturated fatty acids.

Synthetic drugs useful in the methods of the present invention as anti-cytokine agents include, for example, pentoxifylline, rodipram, cyclosporin A, chlorpromazine, thalidomide, antisense oligonucleotides, tetravalent guanylhydrazone (CNI-1493), and bicyclic imidazoles (SK&F 86002).

Inhibition of cytokine (MCP and MIP) synthesis can be achieved by several means: (1) inhibition of transcription; (2) decrease of the mRNA half-life; and (3) inhibition of translation. Phosphodiesterase inhibitors pentoxifylline act mainly on transcription. Dexamethasone inhibits translation. Thalidomide specifically decreases the half-life of cytokine mRNA. Furthermore, antisense oligonucleotides allow specific suppression of MCP and MIP translation.

In certain embodiments, small molecules or other agents that target MCP-1, MIP-1α, or the CCR-2 receptor are employed. A number of groups have described the development of small molecule antagonists of MCP-1 that may be employed to treat PPS or CPPS (e.g., Bharat K. Trivedi, et al, Ann. Reports Med. Chem. 2000, 35, 191, herein incorporated by reference). Workers at Teijen and Combichem reported the use of cyclic amines as MCP-1 antagonists (Tatsuki Shiota, et al., WO 99/25686; Tatsuki Shiota, et al., WO 00/69815, all of which are herein incorporated by refernece) and MIP-1α antagonists (Christine Tarby and Wilna Moree, WO 00/69820, all of which are herein incorporated by reference). Some of these compounds are distinguished by the requirement for the central cyclic amine grouping.

A number of other groups have also described the development of small molecule antagonists of the MCP-1/CCR-2 interaction which may be used to treat PPS or CPPS. Exemplary compounds include, but are not limited to: indolopiperidines (Ian T. Forbes, et al., Bioorg. Med. Chem. Lett. 2000, 10, 1803, herein incorporated by refernece), spiropiperidines (Tara Mirzadegan, et al., J. Biol. Chem. 2000, 275, 25562, wherein incorporated by reference), quaternary amines (Masanori Baba, et al., Proc. Natl. Acad. Sci. 1999, 96, 5698, herein incorporated by reference), 2-substituted indoles (Alan Faull and Jason Kettle, WO 00/46196; Andrew John Barker, et al., WO 99/07351; Andrew John Barker, et al., WO 99/07678; all of which are herein incorporated by reference), pyrazolone derivatives (Janak Khimchand Padia, et al., U.S. Pat. No. 6,011,052, both of which are herein incorporated by reference), 2-substituted benzimidazoles (David Thomas Connor, et al., and WO 98/06703, both of which are herein incorporated by reference), N,N-dialkylhomopiperazines (T. Shiota, et al., and WO 97/44329, both of which are herein incorporated by reference), bicyclic pyrroles (Andrew J. Barker, et al., WO 99/40913, Andrew J. Barker, et al., WO 99/40914; all of which are herein incorporated by reference), and 5-aryl pentadienamides (K. G. Carson, et al., Cambridge Health Tech Institute Chemokine Symposium, McLean, Va., USA, 1999, herein incorporated by reference).

In certain embodiments, the agent employed is a peptide antagonist called MCP-1(9-76) (see Jiang-Hong Gong, et al., J. Exp. Med., 1997, 186, 131, herein incorporated by reference). In other embodiments, the agent employed is interferon b-1b (see, Iarlori et al., J. Neuroimmunol., 2002, 123, 170-179, herein incorporated by reference). In further embodiments, the agent employed is antibody ABN912 from Novartis (see, Haringman, et al., Arthritis and Rheumatism 54, 2006, herein incorporated by reference).

In certain embodiments, the agent employed to treat PPS or CPPS is an indolopiperidine selected from the following:

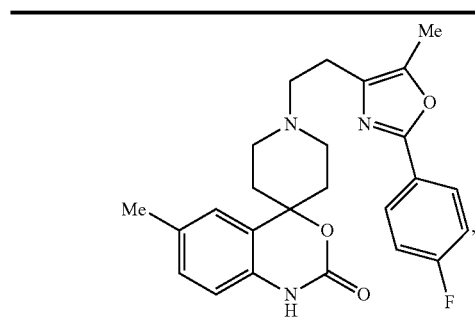

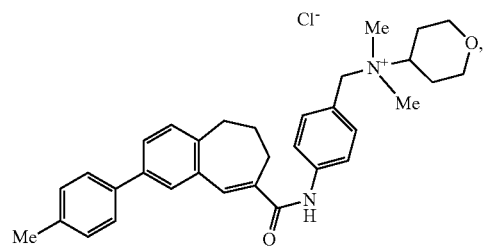 [SMILES: [Cl-] ; Cc1ccc(-c2ccc3c(c2)C=C(C(=O)Nc2ccc(C[N+](C)(C)C4CCOCC4)cc2)CCC3)cc1]

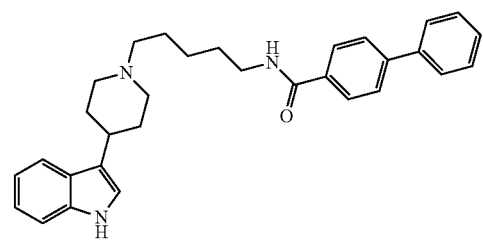 [SMILES: O=C(NCCCCCN1CCC(c2c[nH]c3ccccc23)CC1)c1ccc(-c2ccccc2)cc1]

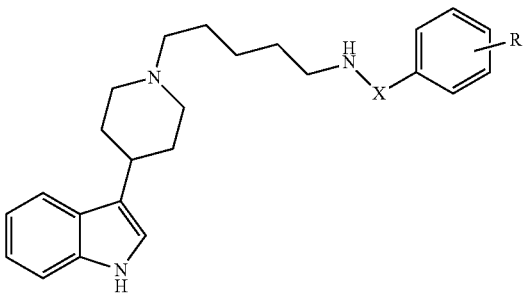

| # | X | R | $K_i$ (nM)[12] |
|---|---|---|---|
| 3 | C=O | 4-Ph | 5400 |
| 8 | C=O | 4-Br | 7100 |
| 9 | C=O | 3,4-diCl | 5100 |
| 10 | $SO_2$ | 3,4-diCl | >10,000 |
| 11 | C(=O)$CH_2$ | 3,4-diCl | 4400 |
| 12 | C(=O)$CH_2CH_2$ | 3,4-diCl | 5900 |
| 13 | C(=O)NH | 3,4-diCl | 1600 |
| 14 | trans C(=O)CH=CH | 3,4-diCl | 420, |

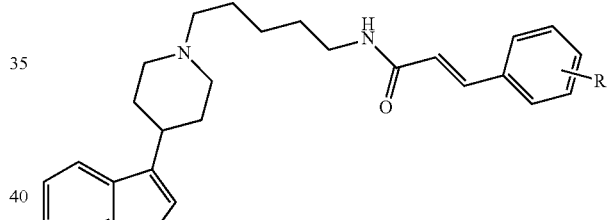

| # | R | $K_i$ (nM)[12] |
|---|---|---|
| 14 | 3,4-diCl | 420 |
| 15 | H | 870 |
| 16 | 4-Cl | 520 |
| 17 | 3-Cl | 560 |
| 18 | 2-Cl | 4400 |
| 19 | 4-Br | 350 |
| 20 | 4-I | 460 |
| 21 | 3-$CF_3$ | 790 |
| 22 | 4-Me | 550 |
| 23 | 3-Me | 790 |
| 24 | 4-Ph | 1450 |
| 25 | 4-$Bu^t$ | 1700 |
| 26 | 4-$NMe_2$ | 1200 |
| 27 | 4-OH | 6300 |
| 28 | 4-NHAc | 12,900 |
| 29 | 4-CN | 2800, |

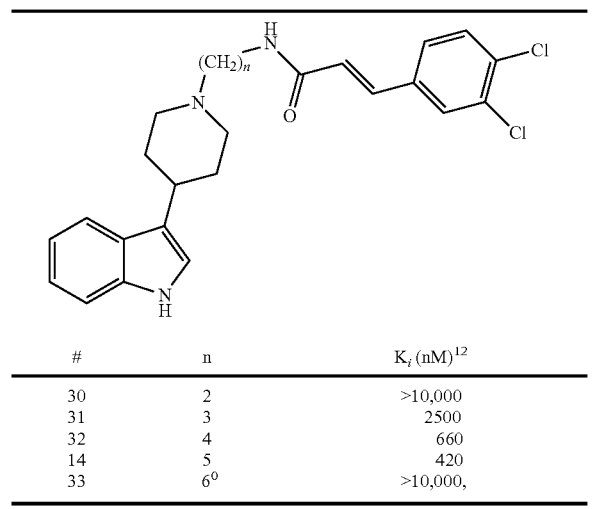

| # | n | $K_i$ (nM)[12] |
|---|---|---|
| 30 | 2 | >10,000 |
| 31 | 3 | 2500 |
| 32 | 4 | 660 |
| 14 | 5 | 420 |
| 33 | 6⁰ | >10,000, |

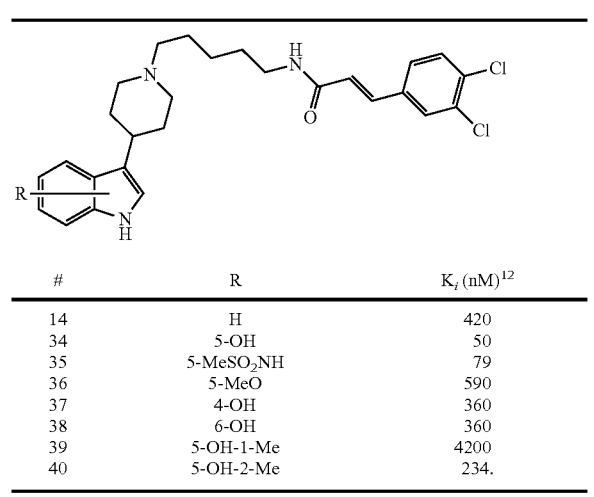

| # | R | $K_i$ (nM)[12] |
|---|---|---|
| 14 | H | 420 |
| 34 | 5-OH | 50 |
| 35 | 5-MeSO$_2$NH | 79 |
| 36 | 5-MeO | 590 |
| 37 | 4-OH | 360 |
| 38 | 6-OH | 360 |
| 39 | 5-OH-1-Me | 4200 |
| 40 | 5-OH-2-Me | 234. |

In other embodiments, the agent employed to treat PPS or CPPS is a spiropiperidine selected from the following:

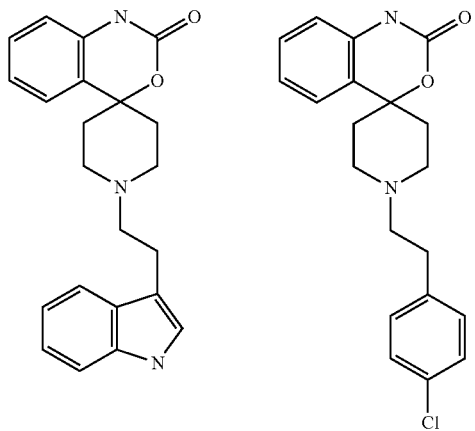

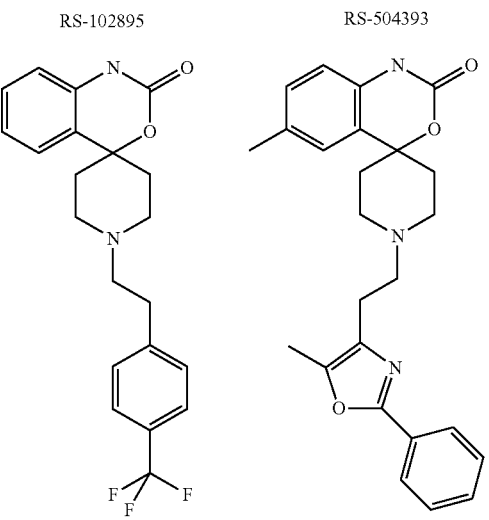

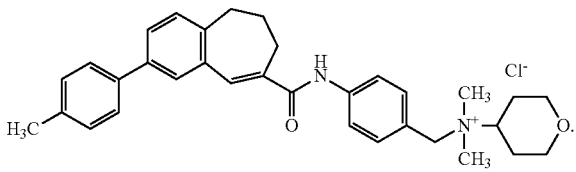 [SMILES: Cc1ccc(-c2ccc3c(c2)C=C(C(=O)Nc2ccc(C[N+](C)(C)C4CCOCC4)cc2)CCC3)cc1 ; [Cl-]]

In particular embodiments, the agent employed to treat PPS or CPPS is a quaternary amine as shown below:

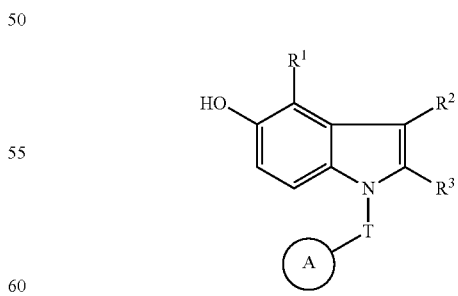

In some embodiments, the agent employed to treat PPS or CPPS is a 2-substituted indole selected from the following:

where $R^1$ is hydrogen, halo or methoxy; $R^2$ is hydrogen, halo, methyl, ethyl or methoxy;
$R^3$ is carboxy, tetrazolyl or —CONHSO$_2$R$^4$ where $R^4$ is methyl ethyl, phenyl, 2,5-dimethylisoxazolyl or trifluoromethyl; T is —CH$_2$— or —SO$_2$—; and ring A is 3-chlorophenyl, 4-chlorophenyl, 3-trifluoromethylphenyl, 3,4-dichloropheny 1,3,4-diffuorophenyl, 3-fluoro-4-chlorophenyl, or 3-chloro-4-fluorophenyl or 2,3-dichloropyrid-5-yl In some embodiments, the agent employed to treat PPS or CPPS is a pyrazolone derivative selected from the following:

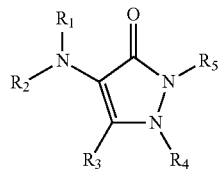

where: $R_1$, $R_2$, $R_3$, $R_4$, $R_5$ can be independently
H,
$C_{1-20}$ alkyl,
$C_{5-7}$ cycloalkyl,
—$(CH_2)_n NR_6 R_7$
—$(CH_2)_{0-6} CONR_6 R_7$,
—$(CH_2)_n OH$ or
—$(CH_2)_{0-6} CO_2 R_{11}$,
biphenyl,
aryl of from 6 to 10 carbon atoms, or
aryl of from 6 to 10 carbon atoms substituted up to 3 times by
    halogen, —CH, lower alkyl of from 1-4 carbon atoms,
    —OH, nitro, —$SO_2H$, $SO_2$ lower alkyl,
    —$SO_2NR_6R_7$ lower alkoxy
    —$CO_2R_{11}$,
    —$CONR_6R_7$,
    —$NR_6R_7$ or $CH_2OH$.

In particular embodiments, the agent employed to treat PPS or CPPS is a 2-substituted benzimidazole selected from the following:

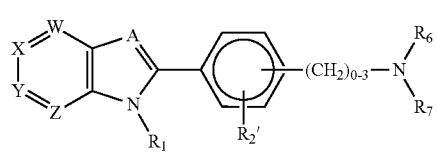

(I)

Benzimidazole derivatives of formula (I) or a pharmaceutically acceptable salt thereof are MCP-1 antagonists are thus useful in the treatment of inflammation, atherosclerosis, restenosis, and immune disorders such as arthritis and transplant rejection wherein A is N or CH; where W, X, Y and Z can be independently C—$R_2$, C—$R_3$, C—$R_4$, C—$R_5$, or N; no more than two of W, X, Y and Z can be N in any one structure, $R_2$, $R_3$, $R_4$, $R_5$ can be independently H, $C_{1-20}$ alkyl, halogen, nitro, —$SO_2NR_8R_9$, alkoxy of from 1-4 carbon atoms; —$S(O)_pR$ where p is an integer from 0 to 2; —$(CH_2)_m OR$, —$(CH_2)_m COOR$, —$(CH_2)_m NR_8R_9$, —$(CH_2)_m CONR_8R_9$, —$(CH_2)_m COR$, or —$CF_3$; m is an integer of from 0 to 4, R is hydrogen, lower alkyl of from 1-4 carbon atoms, aryl of from 6-10 carbon atoms, or benzyl; $R_1$ can be H, lower alkyl of from 1-4 carbon atoms, or —$(CH_2)_m$-Ph; $R_6$ is alkyl of from 1-6 carbon atoms or $R_7$; $R_7$ is $(CH_2)_n NR_{10} R_{11}$; n is an integer from 2 to 6; $R_8$ and $R_9$ can be independently hydrogen, lower alkyl of from 1-4 carbon atoms, or can be taken together to form a ring of from 3-8 atoms have up to one additional heteroatom as O, S, $SO_2$, or N—$R_{12}$; $R_{10}$ and $R_{11}$ can be independently lower alkyl, —$(CH_2)_m$-Ph, unsubstituted or substituted with up to three $R_2$ substituents, or $R_{10}$ and $R_{11}$ can be taken together to form a ring of from 3-8 atoms which may contain oxygen or $NR_{12}$; $R_{12}$ is hydrogen, lower alkyl, —$(CH_2)_t$-Ph, where Ph is phenyl unsubstituted or substituted with up to three $R_2$ substituents; t is an integer of from 0 to 2.

In certain embodiments, the agent employed to treat PPS or CPPS is a N,N-dialkylhomopiperazine selected from the following:

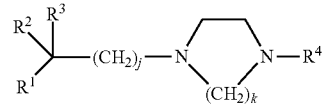

[wherein $R^1$ and $R^2$ are identical to or different from each other representing a phenyl group or an aromatic heterocyclic group having 1-3 heteroatoms selected from oxygen atoms, sulfur atoms, and/or nitrogen atoms, in which the phenyl or aromatic heterocyclic group may be substituted by any number of halogen atoms, hydroxy groups, $C_1$-$C_6$ lower alkyl groups, $C_1$-$C_6$ lower alkoxy groups, phenyl groups, benzyl groups, phenoxy groups, methylenedioxy groups, $C_1$-$C_6$ hydroxyalkyl groups, carboxy groups, $C_2$-$C_7$ elkoxycarbonyl groups, $C_2$-$C_7$ alkanoylamino groups, dioxolanyl grpoups, or by group represented by the formula: —$NR^5R^6$, or else may be condensed with a benzene ring to form a condensed ring, furthermore above substituents for the phenyl or aromatic heterocyclic group and the condensed ring condensed with a benzene ring are optionally substituted by any substituents independently selected from halogen atoms, hydroxy groups, or $C_1$-$C_6$ lower alkoxy groups, and $R^5$ and $R^6$ may be identical to or different from each other representing hydrogen atoms. $C_1$-$C_6$ lower alkyl groups, or $C_2$-$C_6$ lower alkenyl groups;

$R^3$ represents a hydrogen atom, hydroxy group, cyano group, $C_1$-$C_4$ lower alkoxy group or $C_2$-$C_7$ lower alkanoyloxy group:

j represents en integer of 0-3;

k represents 2 or 3;

$R^4$ is a group represented by:

1) Formula: -$A^1$-$R^7$ (in the formula, $R^7$ represents a phenyl group which may be substituted by any number of the same or different (halogen atoms, hydroxy groups, amino groups, $C_1$-$C_6$ lower alkyl groups, $C_1$-$C_6$ lower alkoxy groups, cyano groups, nitro groups, trifluoromethyl groups, $C_1$-$C_7$ alkoxycarbonyl groups, $C_2$-$C_7$ alkanoyl groups, $C_1$-$C_6$ alkylsulfonyl groups, trifluoromethylsulfonyl groups, phenylsulfonyl groups (which may be substituted with a hydroxy group), 1-pyrrolylsulfonyl groups, $C_5$-$C_6$ hydroxyalkylsulfonyl groups, $C_1$-$C_4$ alkanoylamino groups, or a group represented by the formula: —$CONR^8R^9$) in which $R^8$ and $R^9$, identical to or different from each other, represent hydrogen atoms or $C_1$-$C_6$ lower alkyl groups; $A^1$ is a group represented by the formula —$(CH_2)_n$— or a group represented by formula: $(CH_2)_p$-G-$(CH_2)_q$— in which C represents $G^2$ or $G^2$; $G^1$ represents —O—, —CO—, —$SO_2$—, —CO—O—, —CONH—, —NHCO—, —NHCONH—, or —NH—$SO_2$—; $G^2$ represents —(C═NH)NH—$SO_2$—, —CO_NH—NH—CO—, —CO—NH—NH—CO—$NR^{10}$—, —CO—NH-$CH_2$—CO—, —CO—NH—NH—$SO_2$—, or —CO—N($CH_2$—CO—$OCH_3$)—NH—CO—: $R^{10}$ represents a hydrogen at or a phenyl group; m is an integer of 0-3; p is an integer of 1-3; q represents 0 or 1);

In further embodiments, the agent employed to treat PPS or CPPS is a bicyclic pyrrole selected from the following:

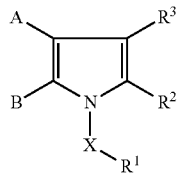

wherein A and B form an optionally substituted alkylene chain so as to form a ring with the carbon atoms to which they are attached; X is $CH_2$ or $SO_2$, $R_1$ is an optionally substituted aryl or heteroaryl ring; $R_2$ is a specified organic group such as carboxy, and $R_3$ is hydrogen or a specified organic group In particular embodiments, the agent employed to treat PPS or CPPS is a cyclic amine derivative selected from the following:

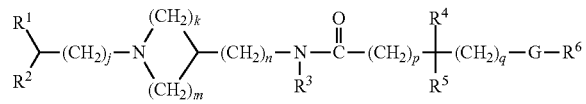

wherein $R^1$ is a phenyl group, a $C_3$-$C_8$ cycloalkyl group, or an aromatic heterocyclic group having 1-3 heteroatoms selected from the group consisting of an oxygen atom, a sulfur atom, a nitrogen atom, or a combination thereof, in which the phenyl or aromatic heterocyclic group may be condensed with a benzene ring or an aromatic heterocyclic group having 1-3 heteroatoms selected from the group consisting of an oxygen atom, a sulfur atom, a nitrogen atom, or a combination thereof, to form a condensed ring, and the phenyl group, $C_3$-$C_8$ cycloalkyl group, aromatic heterocyclic group, or condensed ring may be substituted with one or more of a halogen atom, a hydroxy group, a cyano group, a nitro group, a carboxy group, a carbamoyl group, a $C_1$-$C_6$ alkyl group, a $C_3$-$C_8$ cycloalkyl group, a $C_2$-$C_6$ alkenyl group, a $C_1$-$C_6$ alkoxy group, a $C_1$-$C_6$ alkylthio group, a $C_3$-$C_5$ alkylene group, a $C_2$-$C_4$ alkylenoxy group, a $C_1$-$C_3$, alkylenedioxy group, a phenyl group, a phenoxy group, a phenylthio group, a benzyl group, a benzyloxy group, a benzoylamino group, a $C_2$-$C_7$ alkanoyl group, a $C_2$-$C_7$ alkoxycarbonyl group, a $C_2$-$C_7$ alkanoyloxy group, a $C_2$-$C_7$ alkanoylamino group, a $C_2$-$C_7$ N-alkylcarbamoyl group, a $C_4$-$C_9$ N-cycloalkylcarbamoyl group, a $C_1$-$C_6$ alkylsulfonyl group, a $C_3$-$C_8$ (alkoxycarbonyl)methyl group, a N-phenylcarbamoyl group, a piperidinocarbonyl group, a morpholinocarbonyl group, a 1-pyrrolidinylcarbonyl group, a divalent group represented by the formula: —NH(C=O)O—, a divalent group represented by the formula: —NH(C=S)O—, an amino group, a mono ($C_1$-$C_6$ alkyl)amino group, or a di ($C_1$-$C_6$ alkyl)amino group, wherein the substituent for the phenyl group, $C_3$-$C_8$ cycloalkyl group, aromatic heterocyclic group, or condensed ring is optionally substituted with one or more of a halogen atom, a hydroxy group, an amino group, a trifluoromethyl group, a $C_1$-$C_6$ alkyl group, or a $C_1$-$C_6$ alkoxy group;

$R^2$ is a hydrogen atom, a $C_1$-$C_6$ alkyl group, a $C_2$-$C_7$ alkoxycarbonyl group, a hydroxy group, or a phenyl group, in which the $C_1$-$C_6$ alkyl or phenyl group may be substituted with one or more of a halogen atom, a hydroxy group, a $C_1$-$C_6$ alkyl group, or a $C_1$-$C_6$ alkoxy group, and when j=0, $R^2$ is not a hydroxy group;

j represents an integer of 0-2;
k represents an integer of 0-2;
m represents an integer of 2-4;
n represents 0 or 1;
$R^3$ is a hydrogen atom or a $C_1$-$C_6$ alkyl group optionally substituted with one or two phenyl groups each of which may be substituted with one or more of a halogen atom, a hydroxy group, a $C_1$-$C_6$ alkyl group, or a $C_1$-$C_6$ alkoxy group;

$R^4$ and $R^5$ are the same or different from each other and are a hydrogen atom, a hydroxy group, a phenyl group, or a $C_1$-$C_6$ alkyl group, in which the $C_1$-$C_6$ alkyl group is optionally substituted with one or more of a halogen atom, a hydroxy group, a cyano group, a nitro group, a carboxy group, a carbamoyl group, a mercapto group, a guanidino group, a $C_3$-$C_8$ cycloalkyl group, a $C_1$-$C_6$ alkoxy group, a $C_1$-$C_6$ alkylthio group, a phenyl group optionally substituted with one or more of a halogen atom, a hydroxy group, a $C_1$-$C_6$ alkyl group, a $C_1$-$C_6$ alkoxy group, or a benzyloxy group, a phenoxy group, a benzyloxy group, a benzyloxycarbonyl group, a $C_2$-$C_7$ alkanoyl group, a $C_2$-$C_7$ alkoxycarbonyl group, a $C_2$-$C_7$ alkanoyloxy group, a $C_2$-$C_7$, alkanoylamino group, a $C_2$-$C_7$ N-alkylcarbamoyl group, a $C_1$-$C_6$ alkylsulfonyl group, an amino group, a mono ($C_1$-$C_6$ alkyl)amino group, a di ($C_1$-$C_6$ alkyl)amino group, or an aromatic heterocyclic group having 1-3 of heteroatoms selected from the group consisting of an oxygen atom, a sulfur atom, a nitrogen atom, or a combination thereof and optionally condensed with benzene ring, or $R^4$ and $R^5$ taken together form a 3 to 6 membered cyclic hydrocarbon;

p represents 0 or 1;
q represents 0 or 1;
G is a group represented by —CO—, —$SO_2$—, —CO—O—, —$NR^7$—CO—, —CO—$NR^7$—, —NH—CO—NH—, —NH—CS—NH—, —$NR^7$—$SO_2$—, —$SO_2$—$NR^7$—, —NH—CO—O—, or —O—CO—NH—, wherein $R^7$ is a hydrogen atom or a $C_1$-$C_6$ alkyl group, or $R^7$ taken together with $R^5$ represents $C_2$-$C_5$ alkylene group;

$R^6$ is a phenyl group, a $C_3$-$C_8$ cycloalkyl group, a $C_3$-$C_8$ cycloalkenyl group, a benzyl group, or an aromatic heterocyclic group having 1-3 heteroatoms selected from the group consisting of an oxygen atom, a sulfur atom, a nitrogen atom, or a combination thereof, in which the phenyl, benzyl, or aromatic heterocyclic group may be condensed with a benzene ring or an aromatic heterocyclic group having 1-3 heteroatoms selected from the group consisting of an oxygen atom, a sulfur atom, a nitrogen atom, or a combination thereof, to form a condensed ring, and the phenyl group, $C_3$-$C_8$ cycloalkyl group, $C_3$-$C_8$ cycloalkenyl group, benzyl group, aromatic heterocyclic group, or condensed ring may be substituted with one or more of a halogen atom, a hydroxy group, a mercapto group, a cyano group, a nitro group, a thiocyanato group, a carboxy group, a carbamoyl group, a trifluoromethyl group, a $C_1$-$C_6$ alkyl group, a $C_3$-$C_6$ cycloalkyl group, a $C_2$-$C_6$ alkenyl group, a $C_1$-$C_6$ alkoxy group, a $C_3$-$C_8$ cycloalkyloxy group, a $C_1$-$C_6$ alkylthio group, a $C_1$-$C_3$ alkylenedioxy group, a phenyl group, a phenoxy group, a phenylamino group, a benzyl group, a benzoyl group, a phenylsulfinyl group, a phenylsulfonyl group, a 3-phenylureido group, a $C_2$-$C_7$ alkanoyl group, a $C_2$-$C_7$, alkoxycarbonyl group, a $C_2$-$C_7$, alkanoyloxy group, a $C_2$-$C_7$ alkanoylamino group, a $C_2$-$C_7$ N-alkylcarbamoyl group, a $C_1$-$C_6$ alkylsulfonyl group, a phenylcarbamoyl group, a N,N-di ($C_1$-$C_6$ alkyl)sulfamoyl group, an amino group, a mono ($C_1$-$C_6$ alkyl)amino group, a di ($C_1$-$C_6$ alkyl)amino group, a benzylamino group, a $C_2$-$C_7$ (alkoxycarbonyl) amino group, a $C_1$-$C_6$ (alkylsulfonyl)amino group, or a bis($C_1$-$C_6$ alkylsulfonyl)amino group, wherein the substituent for the phenyl group, $C_3$-$C_8$ cycloalkyl group, $C_3$-$C_8$ cycloalkenyl group, benzyl group, aromatic heterocyclic group, or condensed ring is optionally substituted with one or more of a halogen atom, a cyano group, a hydroxy group, an amino group, trifluoromethyl group, a $C_1$-$C_6$ alkyl group, a $C_1$-$C_6$ alkoxy group, a $C_1$-$C_6$ alkylthio group, a mono ($C_1$-$C_6$ alkyl)amino group, or a di($C_1$-$C_6$ alkyl)amino group.

D. Pharmaceutical Compositions

The present invention further provides pharmaceutical compositions (e.g., comprising the antisense or anti-chemokine compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other anti-chemokine agents that function by a non-antisense mechanism. Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

V. Transgenic Animals Expressing CPPS Marker Genes

The present invention contemplates the generation of transgenic animals comprising an exogenous CPPS marker gene of the present invention or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased presence of CPPS like symptoms.

The transgenic animals of the present invention find use in drug (e.g., CPPS therapy) screens. In some embodiments, test compounds (e.g., a drug that is suspected of being useful to treat CPPS) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 (1985)). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 (1976)). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. (1986)). The viral vector system used to introduce the transgene is typically a replication-defective retrovirus carrying the transgene (Jahner et al., Proc. Natl. Acad. Sci. USA 82:6927 (1985)). Transfection is easily and efficiently obtained by culturing the blastomeres on a monolayer of virus-producing cells (Stewart, et al., EMBO J., 6:383 (1987)). Alternatively, infection can be performed at a later stage. Virus or virus-producing cells can be injected into the blastocoele (Jahner et al., Nature 298:623 (1982)). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra (1982)). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 (1990), and Haskell and Bowen, Mol. Reprod. Dev., 40:386 (1995)).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 (1981); Bradley et al., Nature 309:255 (1984); Gossler et al., Proc. Acad. Sci. USA 83:9065 (1986); and Robertson et al., Nature 322:445 (1986)). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 (1988)). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmmol (micromoles); nmol (nanomoles); pmol (picomoles); g (grams); mg (milligrams); μg (micrograms); ng (nanograms); 1 or L (liters); ml (milliliters); μl (microliters); cm (centimeters); mm (millimeters); μm (micrometers); nm (nanometers); and ° C. (degrees Centigrade).

Example 1

Materials and Methods

Patients and Controls

Classification of patients is based on history (IIIa, IIIb, control), symptoms (according to National Institutes of Health-Chronic Prostatitis Index —NIH-CPSI), and expressed prostatic secretions of white blood cells per high power field (EPS wbc/hpf). Evaluation includes a complete history and physical examination, and includes a four-glass urine test as per published protocols (See, e.g., Nadler et al., Journal of Urology, 164:214-218 (2000), herein incorporated by reference in its entirety for all purposes).

Breifly, expressed prostatic secretion (EPS) samples were collected by digital rectal examination (DRE) from men seen in ambulatory clinic who had no urologic disease (controls, n=16), BPH (n=14); CPPS IIIA (greater than or equal to 10 white blood cells per high power field (WBC/hpf) in EPS) (n=18); CPPS IIIB (less than 10 WBC/hpf in EPS) (n=20); or AIP (n=10) (See table). Classification was based on history, symptoms, DRE of the prostate, and WBC/hpf in the EPS. Controls included men undergoing vasectomy or routine urologic evaluations with no history or symptoms of urinary tract inflammation, palpably normal prostates and normal PSA values (less than 4.0 mg./dl.) for patients 50 years of age or older. Men with BPH had typical obstructive voiding symptoms of BPH, palpably enlarged prostates, and, 10 WBC/hpf in EPS. Men with CPPS had a history of at least three months of pelvic or perineal pain and EPS with or without inflammation. AIP patients included men with no prostatic disease and men with BPH and greater than or equal to 10 WBC/hpf in their EPS.

Assays are read at 490 nM in an ELISA plate reader (Molecular Devices Corporation, Sunnyvale, Calif.). It is confirmed that the assays do not cross react with appropriate standards (Nadler et al., Journal of Urology, 164:214-218 (2000)).

Chemokine levels are compared to the NIH-CPSI, age, and EPS wbc/hpf and statistical analysis performed. The first analytic stage consists of comparisons of each CPPS marker measure (e.g., MCP-1, MIP-1α) for patients classified as Ma, Mb and Control, as well as between the combined Cases (IIIa, Mb) vs. Controls using Student's t-test (incorporating unequal variances) (See, e.g., FIG. 1A). These biomarker differences are tested on the log-transformed scale due to their non-normal, skewed distributions (See, e.g., FIG. 1B). As noted in the sample size table (See Table 1, below), a total sample size of 200 is adequate to detect subgroup differences of only 0.5 standard deviation units when one of the subgroups (e.g., controls) is 20% of the total number of patients. In particular, estimates of the standard deviations for log MCP-1 and log MIP-1α ranged from 0.94 to 1.41 in data acquired during development of the present invention, so that subgroup mean differences of 0.5 to 0.7 for these biomarkers are detectable with 80% power.

TABLE 1

Total sample size required to detect a statistically significant difference in biomarkers (MCP-1, MIP-1α) between two subgroups of patients such as IIIa, IIIb, and Controls, assuming overall α = 0.05, power = 80% for a 2-sided test.

| Proportion of men in sub-group 1 | Difference in Means = $\|\mu_1-\mu_2\|$ | | | |
|---|---|---|---|---|
| | $0.50\sigma$ | $0.75\sigma$ | $1.00\sigma$ | $1.25\sigma$ |
| 0.10 | 360 | 160 | 90 | 60 |
| 0.20 | 200 | 90 | 55 | 35 |
| 0.30 | 154 | 70 | 40 | 27 |
| 0.40 | 135 | 63 | 35 | 25 |
| 0.50 | 128 | 58 | 34 | 24 |

The first voided urine specimen represented the urethral washout and was limited to 10 ml. The second voided specimen was collected late in the urinary flow. Prostatic fluid was obtained by digital massage within 10 minutes of voiding and collected in a sterile manner on a glass slide. The fluid was transferred to a cryovial, stored at −20 C for approximately 2 hours and then transferred for storage at −70 C until thawed for analysis. The residual fluid on the slide was placed under a coverslip and examined promptly with the high power (400×) microscopic lens for cells and particles in 3 to 5 fields. The average number of WBC/hpf was recorded. Microscopic examination of the urine sediment was done after centrifugation for approximately 3 minutes. Localization of bacteria was done according to the method of Meares and Stamey (See, e.g., Moreland et al., N Engl J Med, 337: 141, (1997)) using clean collected specimens streaked on blood and MacConkey's agar plates. Standard microbiologic methods were used to quantify and identify all organisms.

Chemokines

ELISA assays are used to measure MCP-1 and MIP-1α in EPS (CYTIMMUNE Sciences, Inc., College Park, Md.) via methods that have been reported (Nadler et al., Journal of Urology, 164:214-218 (2000)). Each assay is performed using dilutions of recombinant human MCP-1 or MIP-1α. Results are compared with a standard curve prepared using the recombinant human cytokines. Values are computed taking the dilution factor into account. When the results of the assayed samples fall under the limit of detection determined by the lowest recombinant cytokine control standard, results are reported as the value of the lowest detectable standard.

In some embodiments, these subgroups are compared with respect to baseline demographic characteristics such as age, and selected clinical and physiologic characteristics, including their NIH-CPSI symptom score (and its separate subscales, especially the pain subscale). All baseline variables with statistically significant differences at the level of p<0.15 are entered into a logistic regression modeling analysis designed to: 1) determine important predictors that will differentiate between those patients classified as IIIa, IIIb, and Controls 2) generate predicted "probabilities" of Cases (IIIa, IIIb) derived from the logistic regression coefficients, which can then serve in the Receiver Operating Characteristic (ROC) curve analysis. From these model-based results, estimates of sensitivity, specificity and predictive accuracy of selected Cutpoints of these biomarkers are then evaluated for diagnostic criteria for CPPS (See, e.g., FIGS. 2 and 3).

In some embodiments, final models are evaluated for their calibration and discrimination characteristics. It is contemplated that calibration is considered the ability of the model to make unbiased estimates of outcome, whereas discrimination is the ability to accurately predict subjects' outcomes. The calibration of the model assesses how well the predictions of the model correspond to the observed outcomes, and is tested by two complementary statistical approaches. In the first approach, the observed outcomes in the data set is compared to predicted outcomes of the prediction model with percent overall agreement (See, e.g., Hosmer and Lemeshow, Applied Logistic Regression.New York, N.Y., John Wiley & Sons, Inc., (1989)). In the second, the Hosmer-Lemeshow statistic is calculated, which compares the predicted probability of an outcome to observed outcome proportions. Similarly, the discrimination of the model is assessed by two complementary tests. First, the observed outcomes in the data set is compared to predicted outcomes of the model by calculating sensitivity, specificity, and predictive values. Second, the area under a receiver-operator-characteristics (ROC) curve is estimated (See, e.g., Hanley and McNeil, Radiology 143:29-36 (1982)). Model validation is carried out to determine whether predicted values from the model are likely to predict responses on subjects not included in the data set used to build the model.

Example 2

Identification of MCP and MIP as Markers for CPPS

Figure 1B:
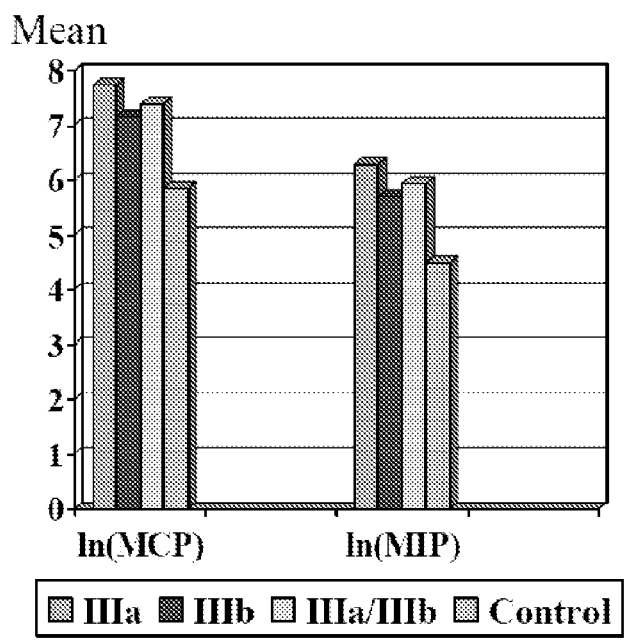

Experiments conducted using the compositions and methods of the present invention indicate that MCP-1 and MIP-1α are significantly elevated in the EPS of patients with both type IIIa and IIIb CPPS compared to controls (See, e.g., FIGS. 1A and 1B). FIG. 1 shows the distribution of the values of MCP and MIP for three groups: Men with chronic prostatitis/chronic pelvic pain syndrome, 1) with inflammation (IIIA), 2) without inflammation (IIIB), and healthy men (the control group). The mean values are significantly higher for the two prostatitis groups as compared to the controls (See, e.g., FIG. 1A, comparing columns for IIIa, IIIb and IIIa/IIIb to control column. The same information composited on a log scale (LN) is also depicted (See, e.g., FIG. 1B). Thus, in some embodiments, the present invention provides markers for CPPS comprising MIP-1α and MCP-1.

Example 3

Classification of CPPS Subjects Using MCP and MIP

Figure 2:
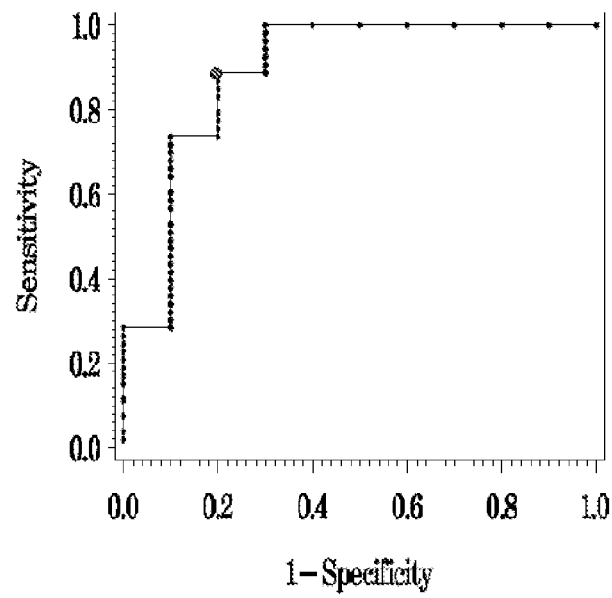
FIG. 2 shows discrimination between case and control using cutpoints of MCP=1061.839 pg/ml and MIP=69.991 pg/ml.
Figure 3:
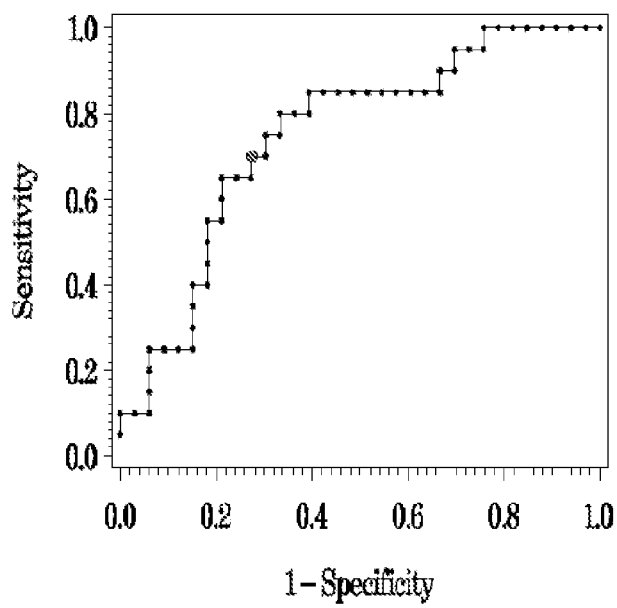
FIG. 3 shows classification of IIIa and Mb using cutpoints of MCP=1061.839 pg/ml and MIP=69.991 pg/ml.

The information generated in Example 2, FIG. 1 was then used to derive what are called "cut points," which are the points that discriminate between cases and controls and give the sensitivity and specificity of these areas (See, e.g., FIGS. 2 and 3). The area under the curve refers to the confidence. The higher that the number approaches one, the more relevant the diagnostic value. For example, in FIG. 2, the area under the curve for the cutpoints described is 0.892, which is excellent. This means that an individual who has a value of MCP-1 of 1061 pg/ml or greater and MIP1a of 70 pg/ml or greater has an 89% chance of having chronic pelvic pain syndrome and there is an 80% chance that he does not have something else. Furthermore, these levels of cytokine expression are biologically significant, that is, they are in the same range of values that are seen in the fluid of, for example, patients with rheumatoid arthritis which is a well recognized disease.

Thus, in some embodiments, the present invention provides detection of and/or measurement of chemokines (e.g., MIP-1α and MCP-1) as indicative of the presence or absence of prostate disease (e.g., CPPS) in a subject. In some embodiments, patients are categorized (e.g., as IIIa and IIIb) and therapies (e.g., anti-chemokine therapies) selected according to the levels of MIP-1α and MCP-1 detected. It is contemplated that, in some embodiments, subjects with certain levels of MIP-1α and MCP-1 (e.g., elevated levels, See, e.g., Example 3, FIGS. 2 and 3), as compared to controls, are classified as possessing prostate disease (CPPS). In some embodiments, being classified as a prostatic disease patient correlates with the likelihood of responding to chemokine directed therapy (e.g. anti-MIP-1α and anti-MCP-1 treatment).

For example, in some embodiments, the compositions and methods of the present invention are utilized to determine the efficacy of potential therapeutic compounds. In some embodiments, patients are evaluated initially, and after undergoing therapy. Since therapeutic trials utilize agents with unknown efficacy, patient response cannot be predicted. However, it is known that approximately 30% of placebo-treated patients show a four-point improvement in their CPSI index. This allows, therefore, the ability to correlate changes in these chemokine markers with the degree of change in CPSI symptoms.

In some embodiments, chemokine assays for MCP-1 and MIP-1α are conducted as noted above. It is contemplated that the MCP-1 and MIP-1α levels will correlate with the CPSI changes and response to therapy. In some embodiments, if the chemokine markers and biomarkers are changed with the symptom response, this indicates that the markers are markers not only for chronic pelvic pain syndrome, but also for an inflammatory environment within the prostate. Thus, in some embodiments, the present invention provides baseline biomarker values (MCP-1, MIP-1α) that are predictors of change in NIH-CPSI over time. For example, in some embodiments, baseline biomarker values are first compared between responders (four or more units of improvement in NIH-CPSI) and non-responders with both treatments combined, as well as within each treatment arm. If there is evidence that any of the biomarkers are statistically significant predictors of treatment response, logistic regression models are used to simultaneously evaluate factors predicting response. In some embodiments, covariates to be considered in these models include patient baseline factors, baseline biomarker values and treatment.

In some embodiments, analysis of changes within groups involve paired comparisons of changes from baseline to primary endpoint, within subgroups defined by treatment arm and/or response to therapy. These analyses utilize Wilcoxon signed rank tests for paired data within each group. Wilcoxon rank-sum tests (for two groups) or Kruskal-Wallis tests (for more than two groups) are used to compare changes among groups. It is contemplated that additional analyses of change from baseline to primary endpoint may be conducted using linear regression models to simultaneously assess the effects of baseline factors, treatment, and response.

Example 4

Treatment of Chronic Pelvic Pain Syndrome

Figure 4:
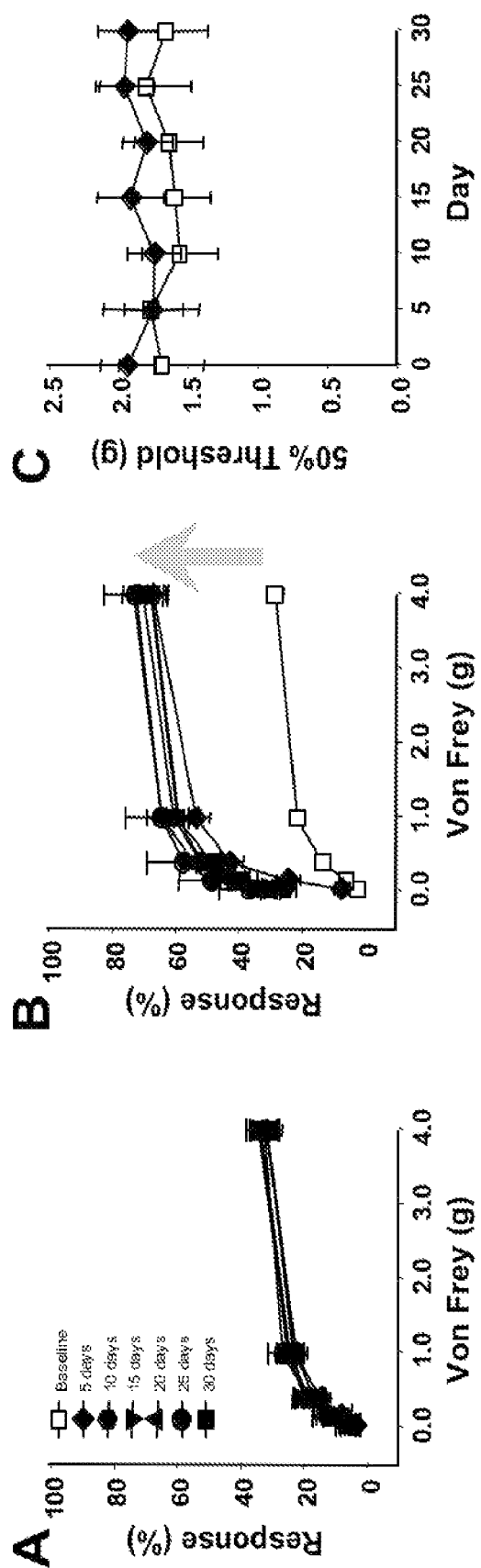
FIG. 4 shows that EAE induces chronic pelvic pain in male NOD mice. Mice were assessed for tactile allodynia with von Frey filaments before and after antigen immunization. Data represent the mean±SEM. A) Sham-injected male NOD mice receiving adjuvant injection (n=10). B) Male NOD mice injected with PAg (n=20). ANOVA exhibited significantly increased responses at all filaments tested in PAg-treated mice at days 10-30 ($p<0.001$), with no significant differences in baseline between controls and PAg-treated mice. C) PAg induced no significant change in tactile sensitivity (50% threshold) of the plantar region of the paw ($p>0.05$ at all times.
Figure 5:
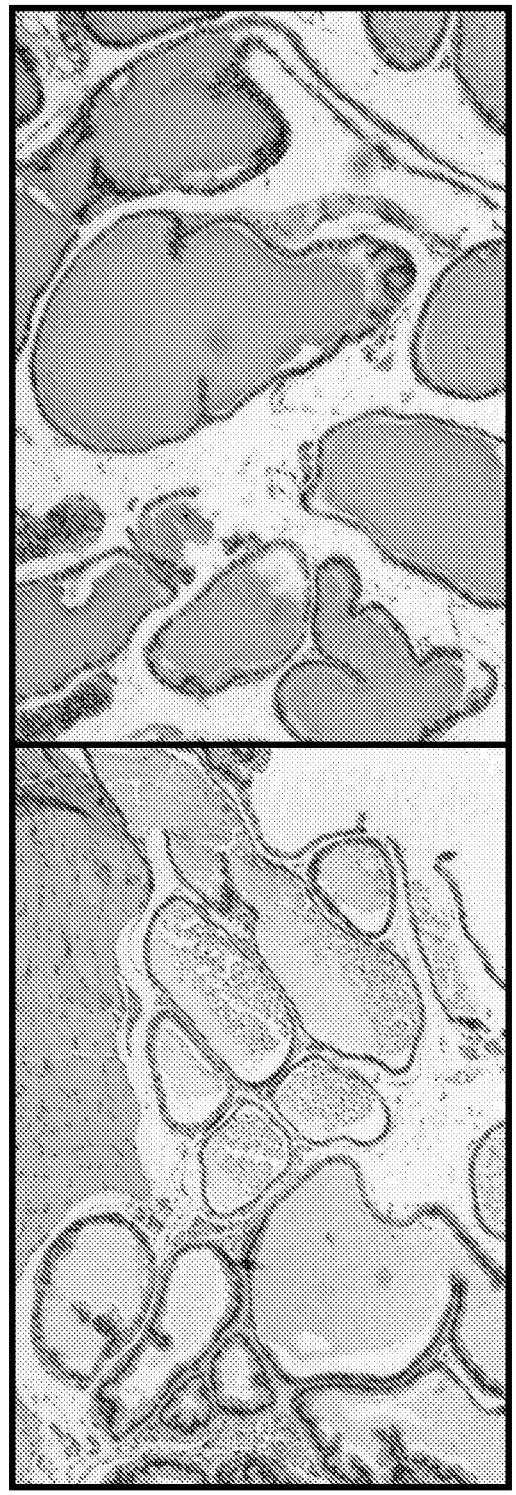
FIG. 5 shows that EAE induces MCP-1 expression in the prostates of male NOD mice. Mice were injected immunized with titermax adjuvant (control) or antigen and prostates were removed after sacrifice 30 days later. Prostate sections were stained with an anti-MCP-1 primary antibody and MCP-1 staining was detected using DAB (brown) followed by haematoxylin counterstain (blue). Prostate sections from EAE animals showed strong MCP-1 staining of prostatic acini that was absent in controls.
Figure 6:
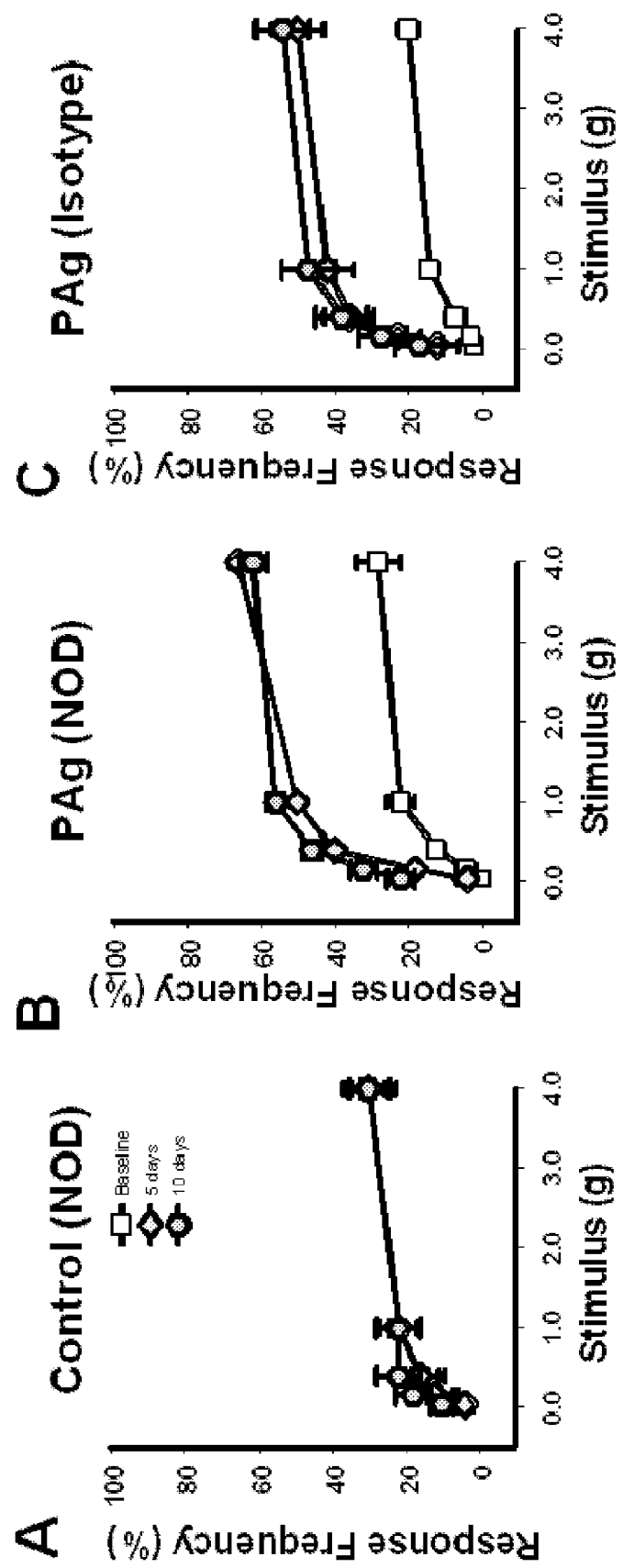
FIG. 6 shows anti-MCP-1 and anti MIP-1 alpha antibody treatment prevents the development of pain in an animal model of pelvic pain. A) Control animals develop no pain at day 5 and day 10. B) Antigen (PAg) induced animals develop pelvic pain at days 5 and 10 post-injection. C) Administration of isotype control antibody (rabbit IgG) does not inhibit pain development. D) & E) Administration of anti-MCP-1 or anti-MIP-1 alpha inhibits pain at days 5 and 10 post-injection. F) Anti-MCP-1 inhibits pain by 68% while anti-MIP-1 alpha inhibits pain by 61% compared to control animals.
Figure 6:
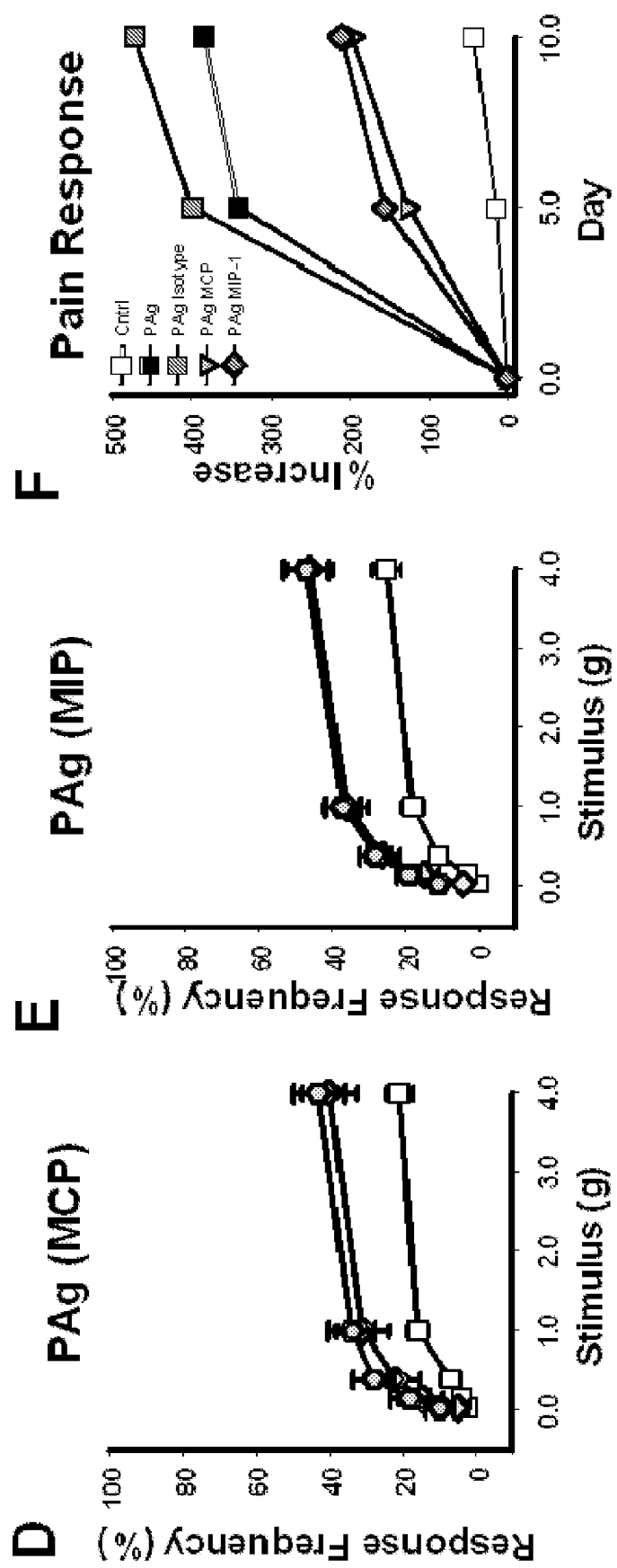

This example describes treatment of an experimental model of CPPS with antibodies to MCP-1. An animal model of experimental autoimmune prostatitis (EAE) that mimics pain symptoms observed in the human disease has previously been described (Rudick, et al., Am J Physiol Regul Integr Comp Physiol, 2008, herein incorporated by reference; see FIG. 4). Using this animal model, it has been successfully demonstrated that pain is localized to pathological changes in the prostate gland and involve inflammation and increased density of nerve fibers in prostatic tissues. This model was used to examine the CP/CPPS diagnostic marker MCP-1, and increased immunohistochemical staining of prostatic acini for MCP-1 was observed (FIG. 5). This increased expression was specific to mice that developed chronic pelvic pain and was absent in mice that showed lack of pain behavior. These results indicate that MCP-1 is involved in the development and pathogenesis of pelvic pain in an animal model of CP/CPPS. It was therefore examined whether anti-MCP-1 therapy could be used to inhibit the development of pelvic pain in the animal model. Commercially derived (R&D systems) polyclonal anti-MCP-1, anti-MIP-1 alpha and an isotype control antibody was used to examine their ability to prevent the development of pelvic pain. Antibodies were administered to NOD mice at the time of initiation of autoimmunity and pain was evaluated at 5 day and 10 days post injection. A significant decrease of 68% in pain responses was observed using the anti-MCP-1, 61% using the anti-MIP-1 alpha and no reduction in pain using the control antibody (FIG. 6). These results show that pelvic pain in this model of CP/CPPS can be inhibited using antibodies targeting MCP-1 and MIP-1 alpha.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of treating a male subject having, or suspected of having, chronic pelvic pain syndrome comprising: treating a male subject with antibodies that bind MCP-1 or MIP-1α, wherein said male subject has one or more symptoms of chronic pelvic pain syndrome, and wherein said treating is under conditions such that at least one of said symptoms is reduced or eliminated.

2. The method of claim 1, wherein said antibodies comprise anti-MCP-1 monoclonal antibodies.

3. The method of claim 1, wherein said antibodies comprise anti-MIP-1α monoclonal antibodies.

4. The method of claim 1, wherein said antibodies comprise polyclonal antibodies that bind MCP-1.

5. The method of claim 1, wherein said antibodies comprise polyclonal antibodies that bind MIP-1α.

6. A method of diagnosing and treating chronic pelvic pain syndrome comprising:
    a) detecting elevated expression of a MCP-1 polypeptide and/or a MIP-1α polypeptide in a sample from a male subject, wherein said male subject has one or more symptoms of chronic pelvic pain syndrome, and wherein said sample comprises semen, seminal fluid, and/or an expressed prostatic secretion from said male subject; and
    b) treating said male subject with antibodies that bind MCP-1 or MIP-1α, wherein said treating is under conditions such that at least one of said symptoms is reduced or eliminated.

7. The method of claim 6, wherein said chronic pelvic pain syndrome is non-inflammatory chronic pelvic pain syndrome.

8. The method of claim 6, wherein said sample comprises an expressed prostatic secretion sample from said subject.

9. The method of claim 8, wherein said expressed prostatic secretion sample comprises less than 10 white blood cells per 400× high power field.

10. The method of claim 6, wherein said detecting comprises detecting an elevated level of expression of said MIP-1α polypeptide in said sample.

11. The method of claim 6, wherein said subject is a human subject.

12. The method of claim 6, wherein said sample comprises said expressed prostatic secretion.

13. The method of claim 6, wherein said antibodies comprise anti-MCP-1 monoclonal antibodies or anti-MIP-1α monoclonal antibodies.

14. A method of treating chronic pelvic pain syndrome comprising:
    a) providing a male subject with one or more symptoms of chronic pelvic pain syndrome, wherein said subject is known to express elevated levels of MCP-1 and/or MIP-1α in their semen, seminal fluid, or prostatic secretions; and
    b) treating said male subject with antibodies that bind MCP-1 or MIP-1α, wherein said treating is under conditions such that at least one of said symptoms is reduced or eliminated.

* * * * *